(12) United States Patent
Jacobs et al.

(10) Patent No.: US 11,364,360 B2
(45) Date of Patent: *Jun. 21, 2022

(54) INVERTED CONTAINER HYDROSTATIC VENTILATOR APPARATUS

(71) Applicant: The Government of the United States of America, as represented by the Secretary of Homeland Security, Washington, DC (US)

(72) Inventors: Bryson Jacobs, Quaker Hill, CT (US); Savannah Lyle, Saint Petersburg, FL (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/527,904

(22) Filed: Nov. 16, 2021

(65) Prior Publication Data

US 2022/0072262 A1    Mar. 10, 2022

Related U.S. Application Data

(63) Continuation of application No. 17/244,728, filed on Apr. 29, 2021, now Pat. No. 11,197,972, which is a
(Continued)

(51) Int. Cl.
*A61M 16/16* (2006.01)
*A61M 16/00* (2006.01)
*A61M 16/20* (2006.01)

(52) U.S. Cl.
CPC ........ *A61M 16/16* (2013.01); *A61M 16/0003* (2014.02); *A61M 16/208* (2013.01); *A61M 2205/3348* (2013.01)

(58) Field of Classification Search
CPC .............. A61M 16/16; A61M 16/0003; A61M 16/208; A61M 2205/3348
See application file for complete search history.

(56) References Cited

U.S. PATENT DOCUMENTS

| 3,834,682 A | 9/1974 | McPhee |
| 3,972,326 A * | 8/1976 | Brawn ................... A63B 23/18 |
| | | 482/13 |

(Continued)

FOREIGN PATENT DOCUMENTS

| WO | 0197894 A1 | 12/2001 |
| WO | 2014201513 A1 | 12/2014 |

(Continued)

*Primary Examiner* — Kendra D Carter
*Assistant Examiner* — Jonathan S Paciorek
(74) *Attorney, Agent, or Firm* — Lavanya Ratnam; Kelly G. Hyndman; Robert W. Busby

(57) ABSTRACT

In an example, a ventilator includes an outer container containing liquid, an inverted container submerged in the liquid to provide inverted container space between a closed top and an inner container liquid level; gas supply line to supply breathing gas to the inverted container space; and inhalation line having an inlet in the inverted container space to provide breathing gas to patient. The inverted container moves upward from a first elevation when the inverted container space reaches a hydrostatic delivery pressure and volume of the inverted container space increases. The inverted container stops moving upward and the gas supply line stops supplying when the inverted container reaches a second elevation above the first. Based on a breath demand signal or preset timing, the inhalation line opens to permit flow of breathing gas to the patient at the hydrostatic delivery pressure, lowering the inverted container due to lost buoyancy resulting in sinkage.

25 Claims, 28 Drawing Sheets

Related U.S. Application Data continuation of application No. 17/096,479, filed on Nov. 12, 2020, now Pat. No. 11,033,706.

(60) Provisional application No. 63/030,005, filed on May 26, 2020.

(56) References Cited

U.S. PATENT DOCUMENTS

| | | |
|---|---|---|
| 4,228,795 A | 10/1980 | Babington |
| 4,303,601 A | 12/1981 | Grimm et al. |
| 4,459,983 A * | 7/1984 | Beyreuther ......... A61M 16/021 137/251.1 |
| 4,597,917 A | 7/1986 | Lunsford |
| 4,941,469 A | 7/1990 | Adahan |
| 8,342,177 B2 | 1/2013 | Porges |
| 9,108,008 B2 | 8/2015 | Stenzler et al. |
| 9,180,265 B2 | 11/2015 | Gutiérrez Fonseca et al. |
| 9,566,409 B2 | 2/2017 | Gründler et al. |
| 9,878,114 B2 | 1/2018 | Daly |
| 9,993,608 B2 | 6/2018 | Cheung et al. |
| 10,279,140 B2 | 5/2019 | Winski |
| 10,449,321 B2 | 10/2019 | Meyerhoff et al. |
| 2005/0279349 A1 | 12/2005 | Patton et al. |
| 2006/0151624 A1 | 7/2006 | Grundler et al. |
| 2011/0252960 A1 | 10/2011 | Bachar |
| 2013/0204151 A1 | 8/2013 | Amirkhanian et al. |
| 2017/0119992 A1 | 5/2017 | Visveshwara et al. |
| 2019/0151597 A1 | 5/2019 | Kwok |
| 2019/0275281 A1 | 9/2019 | Creusot et al. |

FOREIGN PATENT DOCUMENTS

| | | |
|---|---|---|
| WO | 2016157104 A1 | 10/2016 |
| WO | 2019121749 A1 | 6/2019 |
| WO | 2019190332 A1 | 10/2019 |

* cited by examiner

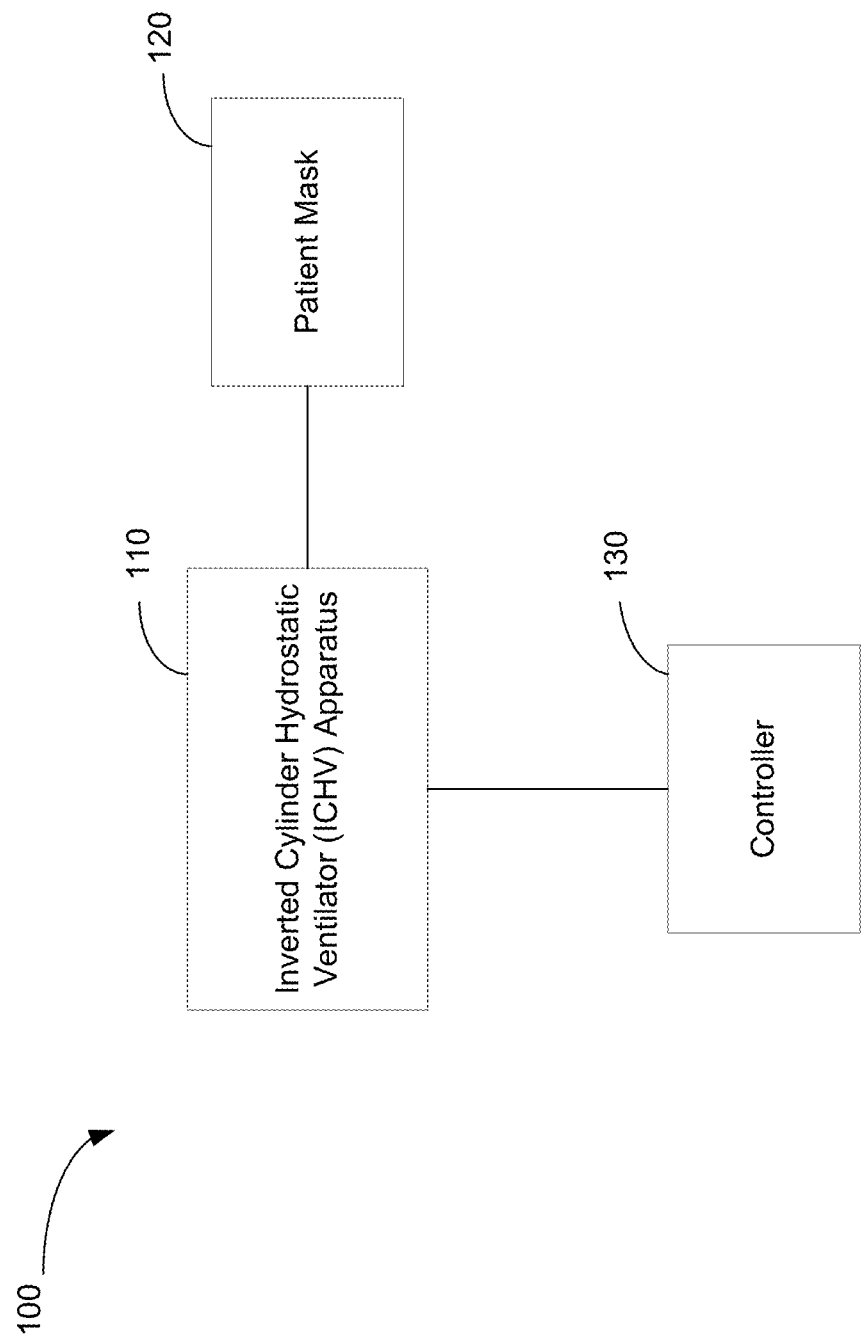

```
// Inverted Cylinder Hydrostatic Ventilator source code

// Based on inner cylinder position, gas injection location, and breathing mode, controls the 5VDC & 12VDC system // manipulators (solenoid valves and air pump, if fitted), via controller & motor shield.

// Momentary buttons are able to manually trigger upper & lower proximity sensors as well as simulate inhalation demand.

// Sensors for inner cylinder proximity and breath demand are activated upon touching ground, due to internal pull ups.

// Rocker switches on breadboard activate the breathing mode and bubbler bypass; LEDs indicate energized states.

// Load the motor shield library and define the outputs
#include <Wire.h>
#include <Adafruit_MotorShield.h>

Adafruit_MotorShield AFMS = Adafruit_MotorShield();

Adafruit_DCMotor *airPump = AFMS.getMotor(1); //air pump(s)
Adafruit_DCMotor *ESV = AFMS.getMotor(2); //expiratory solenoid valve
Adafruit_DCMotor *ISV = AFMS.getMotor(3); //inspiratory solenoid valve
Adafruit_DCMotor *noBub = AFMS.getMotor(4); //bubbler bypass solenoid valve //To keep track of Bubble bypass mode (input) via rocker switch (ON = HIGH = Bypass bubbler).
const int noBubPin = A0;
volatile byte noBubMode;

//To keep track of mode via rocker switch; false = Mandatory breaths, true = Breaths on Demand (input).
```

```
//Need to make mandatory breathing mode a timed function.
const int breatheModePin = A1;
volatile byte breatheMode;

//To keep track of breath demand signal (input) via electrolyte bridge & demandSrc.
const int demandPin = 11;
volatile byte demand;

//Inner cylinder travel sensors tell system when cylinder is at zenith or nadir.
const int SenBot = 7; //bottom sensor input pin
volatile byte V_SenBot; //value assigned to bottom sensor pin
const int SenTop = 9; //top sensor input pin
volatile byte V_SenTop; //value assigned to top sensor pin //To keep track of motion and direction (LOW = DOWNWARD, HIGH = UPWARD)
volatile byte moving;
volatile byte dir;

void setup() {

AFMS.begin();

airPump->run(RELEASE); //air pumps starts OFF
  ISV->run(RELEASE); //ISV starts CLOSED
  ESV->run(FORWARD); //ESV starts OPEN
    ESV->setSpeed(255);
  noBub->run(RELEASE); //bubble bypass solenoid valve starts CLOSED
```

```
// The lower proxy, upper proxy, and breath demand sensors will all be HIGH unless in contact
with ground.
  pinMode(SenBot,INPUT_PULLUP);
  pinMode(SenTop,INPUT_PULLUP);
  pinMode(demandPin,INPUT_PULLUP);
} void loop() {
  // Gather information.
  //Check bubble mode (Switch 'ON' = Bubbler is bypassed)
  noBubMode = digitalRead(noBubPin);

// Check breathing mode (mandatory or on-demand).
  breatheMode = digitalRead(breatheModePin);

// See if top or bottom sensor circuit is energized.
  V_SenTop = digitalRead(SenTop);
  V_SenBot = digitalRead(SenBot);

// Check if a breath is being demanded
  demand = digitalRead(demandPin);

// Evaluate which of the following situations matches the current state & perform actions.
```

FIG. 14C

```
// Cylinder is at the nadir and bubbles are warranted; open GSSV to raise the cylinder using
bubble injection.
  if (V_SenBot == LOW && noBubMode == false) {
    moving = true;
    dir = HIGH;
    airPump->run(FORWARD); //turn on air pump(s).
      airPump->setSpeed(255);
    ISV->run(RELEASE); //close the ISV.
    ESV->run(FORWARD); //open the ESV.
      ESV->setSpeed(255);
    noBub->run(RELEASE); //close the bubble bypass solenoid valve.
  }
// Cylinder is at the nadir and we DON'T want bubbles; open GSSV to raise the cylinder
without bubbles.
  else if (V_SenBot == LOW && noBubMode == true) {
    moving = true;
    dir = HIGH;
    airPump->run(FORWARD); //turn on air pump(s).
      airPump->setSpeed(255);
    ISV->run(RELEASE); //close the ISV.
    ESV->run(FORWARD); //open the ESV.
      ESV->setSpeed(255);
    noBub->run(FORWARD); //open the bubble bypass solenoid valve.
      noBub->setSpeed(255);
  }
```

FIG. 14D

```
// Cylinder is ascending with bubbles. Deleted "V_SenBot == LOW" from conditions; needs to
be tested.
if (moving == true && dir == HIGH && noBubMode == false) {
  airPump->run(FORWARD); //turn on air pump(s).
    airPump->setSpeed(255);
  ISV->run(RELEASE); //close the ISV.
  ESV->run(FORWARD); //open the ESV.
    ESV->setSpeed(255);
  noBub->run(RELEASE); //close the bubble bypass solenoid valve.
}
// Cylinder is ascending WITHOUT bubbles. Deleted "V_SenBot == LOW" from conditions;
needs to be tested.
else if (moving == true && dir == HIGH && noBubMode == true) {
  airPump->run(FORWARD); //turn on air pump(s).
    airPump->setSpeed(255);
  ISV->run(RELEASE); //close the ISV.
  ESV->run(FORWARD); //open the ESV.
    ESV->setSpeed(255);
  noBub->run(FORWARD); //open the bubble bypass solenoid valve.
    noBub->setSpeed(255);
}
```

FIG. 14E

```
// Cylinder has reached Zenith; deactivate GSSV & await further instruction. dir == HIGH to
prevent cutting off air prematurely in demand mode.

if (V_SenTop == LOW && dir == HIGH) { moving = false;

airPump->run(RELEASE); //turn off air pump(s).

ISV->run(RELEASE); //close the ISV.

ESV->run(FORWARD); //open the ESV.

ESV->setSpeed(255);

noBub->run(RELEASE); //close the bubble bypass solenoid valve.

}

// Cylinder is at zenith. Check mode; if mandatory (demand = false), close ESV & open ISV to
sink the cylinder.

if (moving == false && breatheMode == false) { moving = true;

dir = LOW;

airPump->run(RELEASE); //turn off air pump(s).

ISV->run(FORWARD); //open the ISV.

ISV->setSpeed(255);

ESV->run(RELEASE); //close the ESV.

noBub->run(RELEASE); //close the bubble bypass solenoid valve.

```
// Cylinder is at zenith. Check mode; if demand mode is LOW, wait for demand = true, then
close ESV, open ISV to sink the cylinder
else if (moving == false && breatheMode == true && demand == LOW) {
  moving = true;
  dir = LOW;
  airPump->run(RELEASE); //turn off air pump(s).
  ISV->run(FORWARD); //open the ISV.
    ISV->setSpeed(255);
  ESV->run(RELEASE); //close the ESV.
  noBub->run(RELEASE); //close the bubble bypass solenoid valve.
}

// Cylinder is sinking and delivering air.
if (moving == true && dir == LOW) {
  airPump->run(RELEASE); //turn off air pump(s).
  ISV->run(FORWARD); //open the ISV.
    ISV->setSpeed(255);
  ESV->run(RELEASE); //close the ESV.
  noBub->run(RELEASE); //close the bubble bypass solenoid valve.
  }
}
```

FIG. 14G

INVERTED CONTAINER HYDROSTATIC VENTILATOR APPARATUS

CROSS-REFERENCE TO RELATED APPLICATIONS

The application is a continuation of U.S. application Ser. No. 17/244,728, filed Apr. 29, 2021, entitled INVERTED CONTAINER HYDROSTATIC VENTILATOR, which is a continuation of U.S. application Ser. No. 17/096,479, filed Nov. 12, 2020, entitled INVERTED CYLINDER HYDROSTATIC VENTILATOR, which is a nonprovisional of and claims the benefit of priority from U.S. Provisional Patent Application No. 63/030,005, filed on May 26, 2020, entitled INVERTED CYLINDER HYDROSTATIC VENTILATOR, the entire disclosures of which are incorporated herein by reference.

STATEMENT OF GOVERNMENT INTEREST

The present invention was made by employees of the United States Department of Homeland Security in the performance of their official duties. The U.S. Government has certain rights in this invention.

FIELD

The discussion below relates generally to systems and methods of providing mechanical ventilation by moving breathable air into and out of lungs of a patient.

BACKGROUND

A ventilator is a machine that supports breathing by delivering oxygen into the lungs of an individual and removing carbon dioxide from the body. It uses positive pressure to deliver air into the lungs of a patient. The patient may exhale the air or the ventilator can do it for the patient. In a typical system, a mechanical ventilator blows air, or air with increased oxygen, through tubes into the patient's airways. The air flowing to the patient passes through a humidifier, which warms and moistens the air. A mask can be used on the patient's mouth and nose to deliver the air. In some cases, an endotracheal tube goes through the patient's mouth and into the windpipe.

SUMMARY

Embodiments of the present invention are directed to systems and methods for providing mechanical ventilation by moving breathable air into and out of lungs. One type of system employs positive pressure to produce ventilation.

According to specific embodiments, the positive pressure ventilation system is most simply described as a cylinder within a cylinder. A larger cylinder is upright, closed at the bottom and open at the top, and partially filled with water, typically distilled water. A smaller cylinder is inverted, open at the bottom and closed at the top, and immersed in the water bath, trapping air within. Static pressure head can be produced by either introducing more air into the inner cylinder and holding it stationary, thereby pushing the water down and out of its open bottom, or by physically pushing the inner cylinder downward while leaving the amount of trapped air the same. The concept uses both of these principles to produce a steady and metered airflow (the tidal breath) at a prescribed pressure (via downward force exerted on the inner bucket). The inner cylinder vertically reciprocates between a minimum elevation and a maximum elevation, providing breathing air to the patient; the amount of vertical travel determines the volume of air delivered. Adjustable PEEP (Positive End-Expiratory Pressure) is provided via variable-depth exhalation tubing placed into the water bath; the deeper the tube's end, the greater the back pressure against which a patient must exhale.

In some embodiments, the ventilation system employs components that can be fabricated with minimal electronics or no microcontroller, so as to create a low-cost ventilator which can be easily reproduced at remote locations with limited supplies and equipment. Working prototypes have been fabricated, for instance, from flat acrylic sheet ("square" cylinders) or assembled from glass vases exhibiting desirable geometry (approximately 3 to 5 inches in diameter and 16 to 20 inches in height). Plastic resistant to UV-C light is desirable as the primary material, although prefabricated cylinders meeting this and the geometric constraints have been difficult to locate; graduated cylinders ranging from 2 to 4 liters are one possibility.

In accordance with an aspect of the present invention, a ventilator comprises: an outer container having a closed bottom and an open top to contain a liquid inside the outer container; an inverted container having a closed top and an open bottom, the open bottom of the inverted container being submerged in the liquid of the outer container to provide an inner container liquid level inside the inverted container and an outer container liquid level between the inverted container and the outer container, the inverted container including an inverted container wall surrounded by and spaced by an annular space from an outer container wall of the outer container, the open bottom of the inverted container being spaced from the closed bottom of the outer container by an elevation which is variable, the inverted container having an inverted container space between the closed top and the inner container liquid level, the inner container liquid level and the outer container liquid level being measured relative to the closed bottom of the outer container; a gas supply line to supply a breathing gas to the inverted container space; and an inhalation line having an inhalation inlet in the inverted container space and an inhalation outlet outside of the liquid and the inverted container to provide the breathing gas from the inverted container space to a patient. The inverted container is configured to move upward from a preset minimum elevation position when the breathing gas in the inverted container space reaches a hydrostatic delivery pressure and to continue moving upward at the hydrostatic delivery pressure while a volume of the inverted container space increases at the hydrostatic delivery pressure. The inverted container is configured to stop moving upward and the gas supply line being configured to stop supplying the breathing gas to the inverted container space when the inverted container reaches a preset maximum elevation position. Based on one of (1) detection of a patient breath demand signal or (2) a first preset timing, the inhalation line is configured to open to permit a flow of the breathing gas from the inhalation inlet in the inverted container space to the inhalation outlet coupled to the patient at the hydrostatic delivery pressure, lowering the elevation of the inverted container due to lost buoyancy resulting in sinkage. The inhalation line is configured to close and the gas supply line is configured to supply the breathing gas to the inverted container space when the inverted container has reached the preset minimum elevation position, lifting the elevation of the inverted container at the hydrostatic delivery pressure inside the inverted container space.

In accordance with another aspect of the invention, a method of supporting breathing of a patient comprises: placing an inverted container having a closed top and an open bottom in an outer container having a closed bottom and an open top and containing a liquid inside the outer container, the open bottom of the inverted container being submerged in the liquid of the outer container to provide an inner container liquid level inside the inverted container and an outer container liquid level between the inverted container and the outer container, the inverted container including an inverted container wall surrounded by and spaced by an annular space from an outer container wall of the outer container, the open bottom of the inverted container being spaced from the closed bottom of the outer container by an elevation which is variable, the inverted container having an inverted container space between the closed top and the liquid, the inner container liquid level and the outer container liquid level being measured from the closed bottom of the outer container; supplying a breathing gas via a gas supply line to the inverted container space, the inverted container configured to move upward from a preset minimum elevation position when the breathing gas in the inverted container space reaches a hydrostatic delivery pressure and to continue moving upward at the hydrostatic delivery pressure while a volume of the inverted container space increases at the hydrostatic delivery pressure, the inverted container being configured to stop moving upward and the gas supply line being configured to stop supplying the breathing gas to the inverted container space when the inverted container reaches a preset maximum elevation position; placing an inhalation line having an inhalation inlet in the inverted container space and an inhalation outlet outside of the liquid and the inverted container to provide the breathing gas from the inverted container space to the patient; based on one of (1) detection of a patient breath demand signal or (2) a first preset timing, opening the inhalation line to permit a flow of the breathing gas from the inhalation inlet in the inverted container space to the inhalation outlet coupled to the patient at the hydrostatic delivery pressure, lowering the elevation of the inverted container; and closing the inhalation line and supplying the breathing gas via the gas supply line to the inverted container space when the inverted container has reached the preset minimum elevation position, lifting the elevation of the inverted container at the hydrostatic delivery pressure inside the inverted container space.

In accordance with yet another aspect of this invention, a ventilator comprises: an outer container having a closed bottom and an open top to contain a liquid inside the outer container; an inverted container having a closed top and an open bottom, the open bottom of the inverted container being submerged in the liquid of the outer container to provide an inner container liquid level inside the inverted container and an outer container liquid level between the inverted container and the outer container, the inverted container including an inverted container wall surrounded by and spaced by an annular space from an outer container wall of the outer container, the open bottom of the inverted container being spaced from the closed bottom of the outer container by an elevation which is variable, the inverted container having an inverted container space between the closed top and the liquid, the inner container liquid level and the outer container liquid level being measured from the closed bottom of the outer container; a mechanism for directing a breathing gas to the inverted container space, to move the inverted container upward from a preset minimum elevation position when the breathing gas in the inverted container space reaches a hydrostatic delivery pressure, to continue moving the inverted container upward at the hydrostatic delivery pressure while a volume of the inverted container space increases at the hydrostatic delivery pressure, to stop moving the inverted container upward when the inverted container reaches a preset maximum elevation position, and to moving the inverted container upward at the hydrostatic delivery pressure when the inverted container drops from the preset maximum elevation position to the preset minimum elevation position; an inhalation line having an inhalation inlet in the inverted container space and an inhalation outlet outside of the liquid and the inverted container to provide the breathing gas from the inverted container space to a patient; based on one of (1) detection of a patient breath demand signal or (2) a first preset timing, the inhalation line being configured to open to permit a flow of the breathing gas from the inhalation inlet in the inverted container space to the inhalation outlet coupled to the patient at the hydrostatic delivery pressure, lowering the elevation of the inverted container; and the inhalation line being configured to close when the inverted container has reached the preset minimum elevation position.

Other features and aspects of various examples and embodiments will become apparent to those of ordinary skill in the art from the following detailed description which discloses, in conjunction with the accompanying drawings, examples that explain features in accordance with embodiments. This summary is not intended to identify key or essential features, nor is it intended to limit the scope of the invention, which is defined solely by the claims.

BRIEF DESCRIPTION OF THE DRAWINGS

The attached drawings help explain the embodiments described below.

FIG. 1 shows a schematic view of an inverted cylinder hydrostatic ventilator (ICHV) system including an ICHV apparatus.

FIG. 2A shows the ICHV apparatus in an initial charging process from startup State 0 in bubble-conditioning mode.

FIG. 2B shows the ICHV apparatus in a charging process with tidal volume addition to a ready-to-deliver State 1 in bubble-conditioning mode.

FIG. 2C shows the ICHV apparatus in the ready-to-deliver State 1.

FIG. 2D shows the ICHV apparatus in a breath-delivery process from State 1 to a breath-delivered State 2.

FIG. 2E shows the ICHV apparatus in the breath-delivered State 2 ready for charging in non-conditioning mode.

FIG. 2F shows the ICHV apparatus in a charging-and-expiration process from State 2 to State 1 in non-conditioning mode.

FIG. 2G shows the ICHV apparatus in the ready-to-deliver State 1.

FIG. 2H shows the ICHV apparatus in a breath-delivery process from State 1 to State 2.

FIGS. 14A-14G show an example of controller logic for operating an ICHV system according to an embodiment of the invention.

DETAILED DESCRIPTION

Figure 2A:
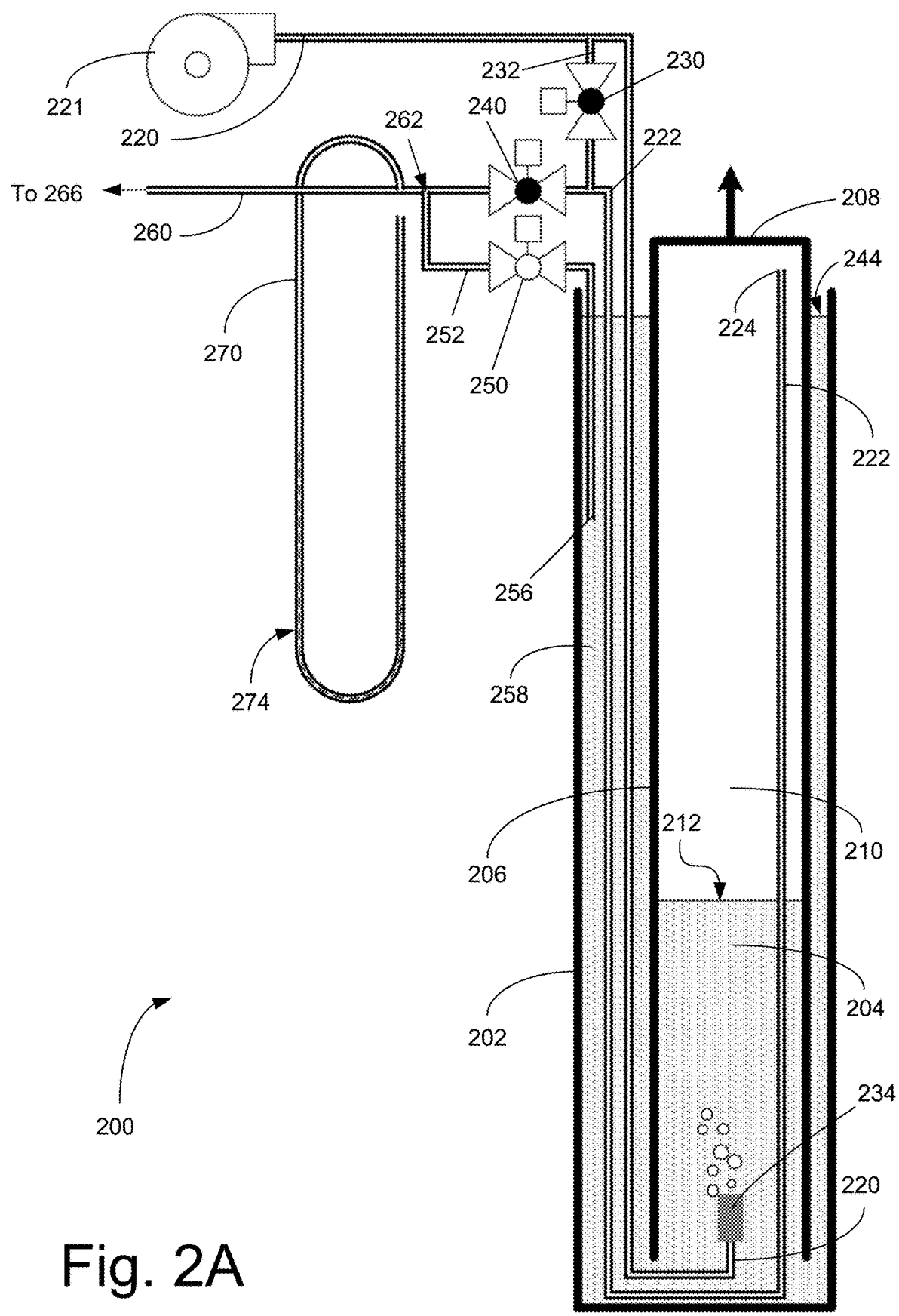
FIGS. 2A-2H schematically illustrate the operation of an ICHV apparatus according to an embodiment.

A number of examples or embodiments of the present invention are described, and it should be appreciated that the present invention provides many applicable inventive concepts that can be embodied in a variety of ways. The embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure along with the knowledge of one of ordinary skill in the art.

The design philosophy according to embodiments of the present invention is to keep the design, its applied physics, and user interface as simple and visually intuitive as possible. The design principles take advantage of water's abilities to provide static pressure head, low-tolerance sealing, humidification and warming, and viral decontamination when treated with ultraviolet (UV) light and/or increased salinity.

In some embodiments, the simplicity and viability of this design concept is realized. It may be low-tech, but it is highly visual to end-operators and reliable with little need for tight tolerances between moving parts. It merely uses the principles of buoyancy, displacement, and gravity through clever geometric manipulation.

ICHV System and Operation

FIG. 1 shows a schematic view of an inverted cylinder hydrostatic ventilator (ICHV) system 100 including an ICHV apparatus 110. The ICHV apparatus 110 is connected to a patient mask 120 to be placed over the patient's face to deliver breathing air to the patient's lungs. A controller 130 may be used to control operation of the ICHV apparatus 110 and delivery of breathing air via the mask 120 to the patient.

ICHV Apparatus

FIGS. 2A-2H schematically illustrate the operation of an ICHV apparatus according to an embodiment. The ICHV apparatus 200 includes an upright outer cylinder 202 having a closed bottom and an open top and containing a water bath 204, and an inverted inner cylinder 206 having an open bottom submerged in the water bath 204 of the upright cylinder or upright container 202 and a closed top 208 above the water bath 204. The inner cylinder 206 is configured to move up and down along guide rails provided inside the upright cylinder 202. The inner cylinder 206 can be restrained from lateral motion by a variety of sliding supports. Vertical guide rails running parallel to the inner cylinder 206 and connected via sliprings is one method. In one example, a 3D printed "lid skid" upon which valves, breath demand manometer, controller, and air pump(s) are mounted; lateral motion of the inner cylinder 206 is arrested by a rigid sleeve of slightly larger diameter than the inner cylinder's outer diameter and extending approximately 12.5 cm down into the outer cylinder 202. The sleeve's length inhibits tipping of the inner cylinder 206 while its loose fit minimizes friction, while rotation about the vertical axis is permitted. Protrusions may extend inward from the outer container wall(s) of the outer cylinder 202 providing resistance to lateral motion and rotation of the inner cylinder 206 while permitting vertical translation.

The inverted cylinder or inverted container 206 includes a gas volume in an inverted cylinder space 210 trapped by the water bath 204 in the upright cylinder 202, in the inverted cylinder space or inverted container space 210 above an inverted inner cylinder free water surface 212. The gas volume in the inverted cylinder space 210 can expand or contract. Adjustable cylinder weights may be disposed on top of the inverted cylinder 206 to control the pressure in the gas volume, which is set by selecting an amount of the weights. The open bottom of the inverted container 206 is spaced from the closed bottom of the outer container 202 by a variable elevation. The inverted container 206 is configured to move upward from a preset minimum elevation position when the breathing gas in the inverted container space 210 reaches a hydrostatic delivery pressure and to continue moving upward at the hydrostatic delivery pressure while a volume of the inverted container space 210 increases at the hydrostatic delivery pressure, the inverted container 206 being configured to stop moving upward when the inverted container 206 reaches a preset maximum elevation position.

In one embodiment, a maximum volume proximity sensor, such as a maximum volume lower limit switch, is disposed at a location above the inverted cylinder 206 to control the maximum gas volume. A minimum volume proximity sensor is disposed at a location below the closed top 208 of the inverted cylinder 206 to control the minimum gas volume. For example, the minimum volume proximity sensor, such as a minimum volume upper limit switch, is located along the guide rails. The minimum volume proximity sensor is tripped (e.g., electrically, magnetically, mechanically, acoustically, or optically) when the inverted cylinder 206 drops to a preset minimum height or elevation level and activates the minimum volume proximity sensor (see FIGS. 5 and 6 below).

When gas is introduced into the inverted cylinder space 210 via a gas supply line or tube 220 (e.g., by an air pump 221), the pressure increases until it is sufficient to expand the gas volume and lift the weight of the inverted cylinder 206 and any weight placed thereon. The pressure is the hydrostatic delivery pressure. During expansion of the gas volume at the hydrostatic delivery pressure via introduction of more gas, the inverted cylinder 206 moves upward and then stops moving upward when the inverted cylinder 206 reaches a preset maximum elevation position or level and the maximum volume proximity sensor or maximum elevation sensor is activated. During contraction of the gas volume at the hydrostatic delivery pressure due to escaping of the gas (via an inhalation tube or patient gas delivery tube 222 as described below), the inverted cylinder 206 sinks downward and then stops moving downward when the minimum volume proximity sensor or minimum elevation sensor is activated. The proximity sensors can be adjusted to set a variable maximum gas volume and/or a variable minimum gas volume, the difference between the two defining the tidal breath. The proximity sensors may be electrically activated by electrical contact, magnetically controlled electrical switches (reed switches), mechanically activated, or ultrasonically or optically ranged and activated, for example.

A bubbler bypass valve (one-way) 230 is provided on a bubbler bypass line or tube 232. The bubbler bypass valve 230 may be closed to allow the breathing gas to be supplied via the gas supply line 220 to a gas supply outlet terminating at a bubbler 234 submerged in the water bath 204 if enhanced humidification is desired in a bubble-conditioning mode. The bubbler 234 is disposed at a location below the inverted inner cylinder free water surface 212 and at or above the open bottom of the inverted cylinder 206, for the breathing gas or breathable gas to egress and bubble up through the water bath 204 prior to entering the trapped gas volume (i.e., bubble mode), thereby serving as a conditioning gas supply outlet.

An inhalation or inspiratory valve or patient gas delivery valve (one-way) 240 is provided on a patient supply (or patient gas delivery) or inhalation line or tube 222 to supply breathing gas, in an opened position, from the inhalation inlet 224 disposed in the gas volume of the inverted cylinder space 210 to the patient.

When the gas supply operates in a non-conditioning mode where bubbles are not desired, the bubbler bypass valve 230 is opened to direct the breathing gas through the inhalation line 222, which now serves as the non-conditioning gas supply line. The breathing gas is flowed directly via the line 222 exiting the non-conditioning gas supply outlet 224 to the inverted cylinder space 210 of the inverted cylinder 206 at the location above the inverted inner cylinder water free surface 212, bypassing the bubbler 234 to preclude the formation of bubbles (i.e., direct injection mode).

The ICHV apparatus 200 is designed to deliver the breathing gas from the gas volume of the inverted cylinder space 210 to the patient at a constant delivery pressure. The prescribed pressure is the target hydrostatic delivery pressure as determined by the total weight of the inner cylinder 206 and any additional weights placed on the inner cylinder 206. When the prescribed pressure (as represented by the outer cylinder water height at the outer cylinder free water surface 244 above the inner cylinder water height at the inner cylinder free water surface 212) is reached, the addition of more breathing gas via the gas supply line will cause the inner cylinder 206 to buoyantly rise until the maximum elevation is reached and the maximum volume proximity sensor is activated. The additional volume introduced into the gas volume of the rising inner cylinder 206 corresponds to a tidal volume. As such, the height of the maximum volume proximity sensor such as a maximum volume lower limit switch determines the delivered tidal volume. The tidal volume is the volume of breathing gas delivered to the patient's lungs with each breath by the ICHV system. Historically, initial tidal volumes were set at 10 to 15 mL/kg of actual body weight for patients with neuromuscular diseases. It can be adjusted by medical professionals for different patients based on their needs.

An exhalation line or tube 252 has an exhalation inlet to receive exhaled gas from the patient and an exhalation outlet 256 to release the exhaled gas. An exhalation or expiratory valve (one-way) 250 is provided on the exhalation line 252 to permit exhaled breath of the patient to flow, in an opened position, from the exhalation inlet coupled to the patient (e.g., via a mask) to the exhalation outlet 256 in the water bath 204 of the upright cylinder 202. The exhalation line 252 terminates at the exhalation outlet 256 at a desired elevation which is selected and fixed for operation at the fixed elevation relative to the closed bottom of the outer container 202, in an annular region 258 between the upright cylinder 202 and the inverted cylinder 206, outside of the inverted cylinder 206. A target hydrostatic backpressure is set by a submerged depth of the exhalation outlet 256 of the exhalation line 252 in the water bath 204, which is the depth measured from the outer container liquid level 244 between the inverted inner cylinder 206 and the upright outer cylinder 202. As such, an adjustable PEEP (Positive End-Expiratory Pressure) is provided via variable-depth exhalation outlet 256 placed into the water bath 204. The depth can be adjusted based on the patient's ventilation need as determined by the medical professionals. The depth can further be changed as the patient's ventilation need changes.

An inhalation valve 240 is disposed in the inhalation line 222 and is configured to be opened to permit the breathing gas to flow from the inhalation inlet 224 to the inhalation outlet or be closed to block the breathing gas from flowing from the inhalation inlet 224 to the inhalation outlet. An exhalation valve 250 disposed in the exhalation line 252 and being configured to be opened to permit an exhalation gas to flow from the exhalation inlet to the exhalation outlet 256 or be closed to block the exhalation gas from flowing from the exhalation inlet to the exhalation outlet 256.

Figure 3A:
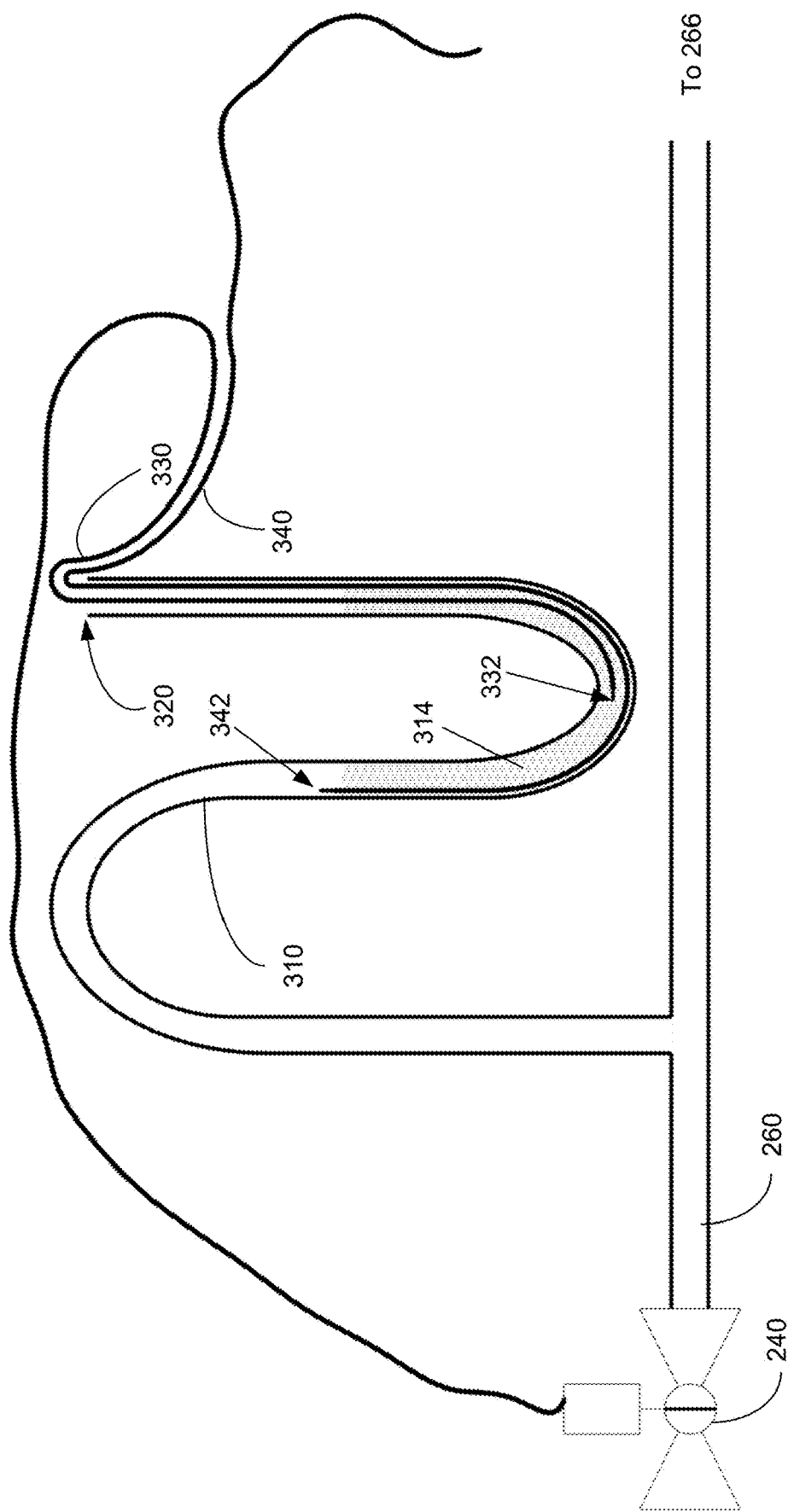
FIG. 3A shows an example of a breath demand mode water switch, for switching on and off of the inhalation valve for on-demand breathing instead of mandatory breathing, in a neutral state.
Figure 3B:
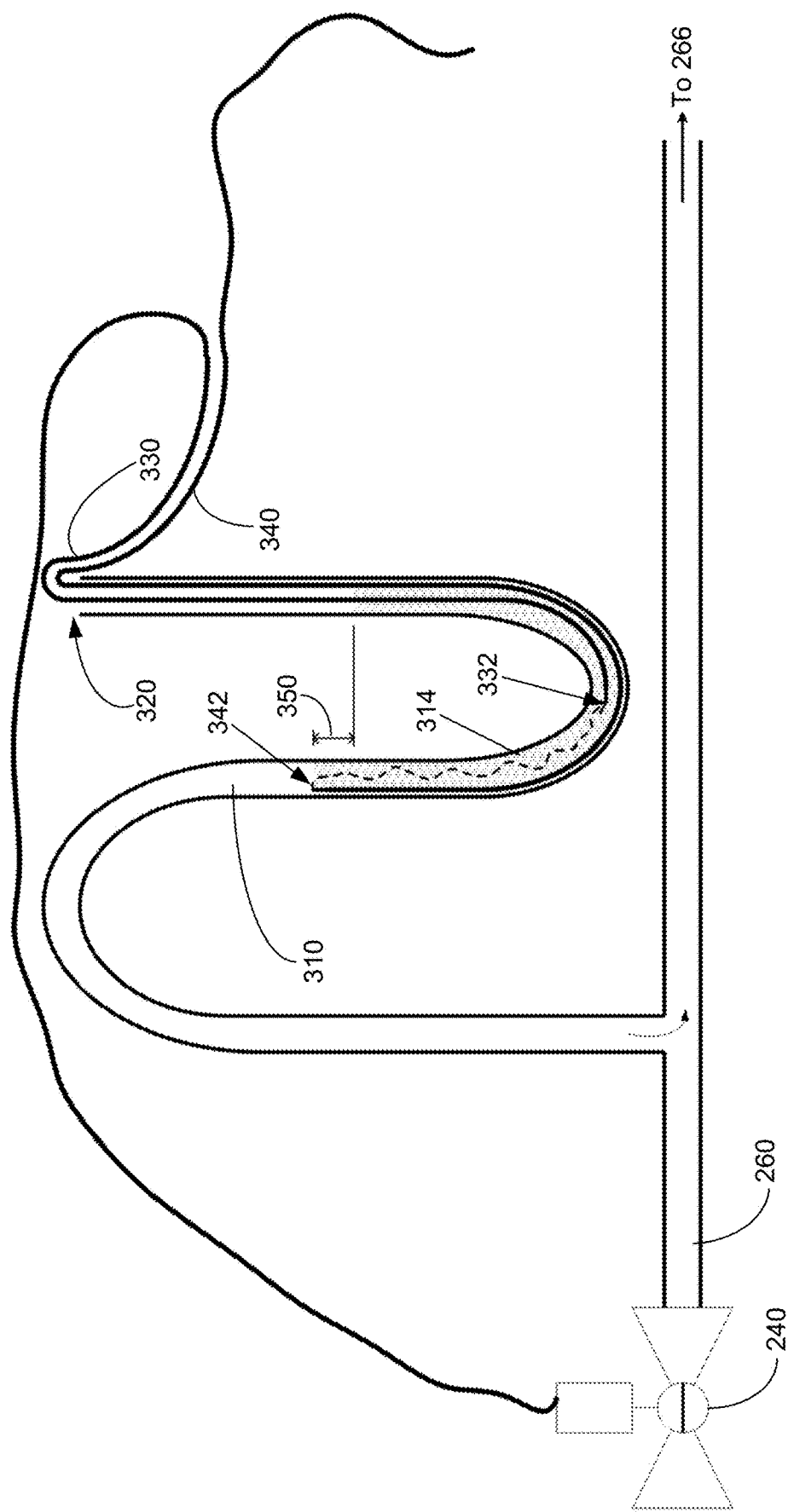
FIG. 3B shows the breath demand mode water switch of FIG. 3A in an active state.

In this embodiment, the inhalation line 222 and the exhalation line 252 merge, outside of the outer and inner cylinders 202, 206, at a junction 262 into a single patient breathing line 260 coupled to the patient (serving as inhalation line when air flows to the patient or exhalation line when air flows from the patient). The junction 262 is disposed downstream of the inhalation valve 240 and upstream of the exhalation valve 250. Disposed between the junction 262 and the patient is a manometer 270 containing a non-toxic electrolytic liquid 274. This is an example of a breath demand mode water switch for switching on and off of the inhalation valve 240 in the inhalation line 222 for on-demand breathing instead of mandatory breathing. The manometer 270 is disposed between the inhalation valve 240 and a breathing line opening 266 of the single patient breathing line 260 coupled to the patient, which is the inhalation outlet during inhalation by the patient and the exhalation inlet during exhalation by the patient. Details of its operation are shown in FIGS. 3A-3B and described below.

The bubbler bypass valve 230, inhalation valve 240, and exhalation valve 250 may be solenoid valves. Solenoid air valves are relatively low-pressure valves operated by a signal from a low-voltage relay. These three valves are turned on and off by the controller based on sensor inputs in the on-demand breathing mode. In contrast, in the mandatory breathing mode, the three valves are all programmed to open and close automatically at specific times in the breathing cycle. The ICHV apparatus of FIGS. 2A-2H is capable of operating in the on-demand breathing mode and the mandatory breathing mode.

There are two hydrostatic pressures of interest in the ICHV apparatus. The first is the delivery pressure of breathing gas delivered from the gas volume in the inverted cylinder space 210 of the inverted cylinder 206 to the patient during inhalation. The second is the necessary exhalation backpressure against which the patient must exhale in order to avoid collapse of the alveoli in the lungs (also known as positive-end expiratory pressure, or PEEP). The depth of the exhalation outlet 256 of the exhalation line 252 determines the amount of PEEP the patient should experience during exhalation (this backpressure is hydrostatically generated). In contrast, the weight of the inner cylinder 206 determines the breathing gas delivery pressure (the more weight, the higher the delivery pressure). This delivery pressure is immediately exhibited by the difference in height between the water's free surface location 244 at an outer container liquid level within the outer cylinder 202 (the annular space 258 between the inner cylinder 206 and the outer cylinder 202) and its free surface 212 within the inner cylinder 206 at an inner container liquid level. The inner container liquid level at the inner cylinder's free surface 212 will always be lower than the outer container liquid level of the outer cylinder's free surface 244 (the height difference corresponds to the hydrostatic delivery pressure). Delivery pressure and available delivered volume exhibit an inverse relationship (i.e., at a higher delivered pressure, less gas will be available for delivery, due to the location of the inverted inner cylinder free water surface 212 being limited by the cylinder's open end rim); therefore, the design's geometric limits should consider the question as to what the largest volume needs to be delivered at the highest pressure. A possible embodiment to increase pressure and volume range could be clamping geometrically similar extensions to the open ends of the inner and outer cylinders, allowing base units to be relatively compact for shipment and less-intensive use, but geometrically expanded for patients requiring more tidal volume, more pressure, or both.

Operation of ICHV Apparatus

FIG. 2A shows the ICHV apparatus in an initial charging process from startup State 0 in the bubble-conditioning mode. In this start-up step, the open bottom of the inverted inner cylinder 206 is submerged inside the water bath 204 of the upright outer cylinder 202 with the gas volume inside the inverted cylinder space 210 above the inverted cylinder free water surface 212. The exhalation outlet 256 of the exhalation line 252 is submerged in the annular space 258 of the water bath 204 between the inner cylinder 206 and the outer cylinder 202 at a submerged depth or elevation selected to set a target hydrostatic backpressure.

The bubbler bypass valve 230 is closed to direct the supply of the breathing gas to flow to the inverted cylinder space 210. The inhalation valve 240 is closed. The exhalation valve 250 is opened so that the patient is free to exhale into the water bath 204 via the exhalation tube 252 having the exhalation outlet end 256 terminating at a preset depth based on the prescribed positive end-expiratory pressure (PEEP). The inverted inner cylinder 206 is neutrally buoyant, at its lowest elevation, and ready to be filled with breathing gas. The breathing gas begins displacing water out of the inverted cylinder 206 and building pressure. In this way, the inverted cylinder 206 is prefilled with breathing gas in the gas volume of the inverted cylinder space 210 to set a delivery pressure (as represented by the outer cylinder water height at the outer cylinder free water surface 244 above the inner cylinder water height at the inner cylinder free water surface 212). The inner cylinder 206 is sensed to be at the preset minimum height. The breathing gas supply source, an air pump 221 in this case, energizes and delivers air to the inverted cylinder 206. When running in bubble-conditioning mode, the system delivers gas to the bottom of the water bath 204 where it passes through the bubbler 234 and ascends into the inner cylinder 206, making it begin to rise.

Figure 2B:
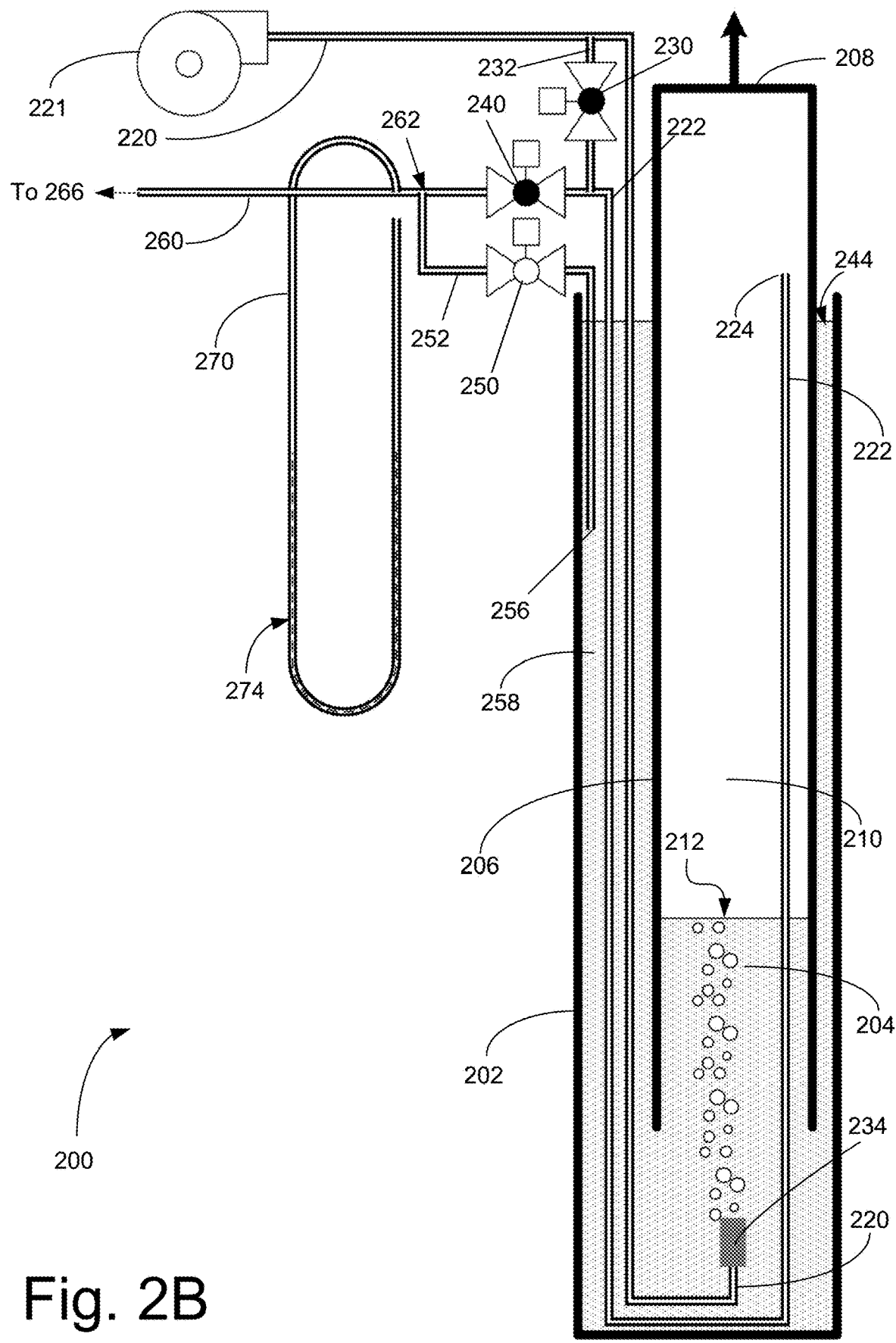

FIG. 2B shows the ICHV apparatus in a charging process in the bubble-conditioning mode, with tidal volume addition as the apparatus progresses to a ready-to-deliver State 1. The air pump 221 continues to deliver air to the inverted cylinder space 210 via the bubbler 234 to form diffused, humidified, and warmed bubbles until the inner cylinder 206 has risen to a preset height based on the prescribed tidal volume to be delivered. The inverted cylinder 206 becomes positively buoyant and rises at constant pressure as breathing gas fills the available gas volume of the inverted cylinder space 210 to add the tidal volume. The patient is still free to exhale into the water bath 204 via the exhalation line 252 with the exhalation outlet 256 at the preset depth based on the prescribed PEEP.

Figure 2C:
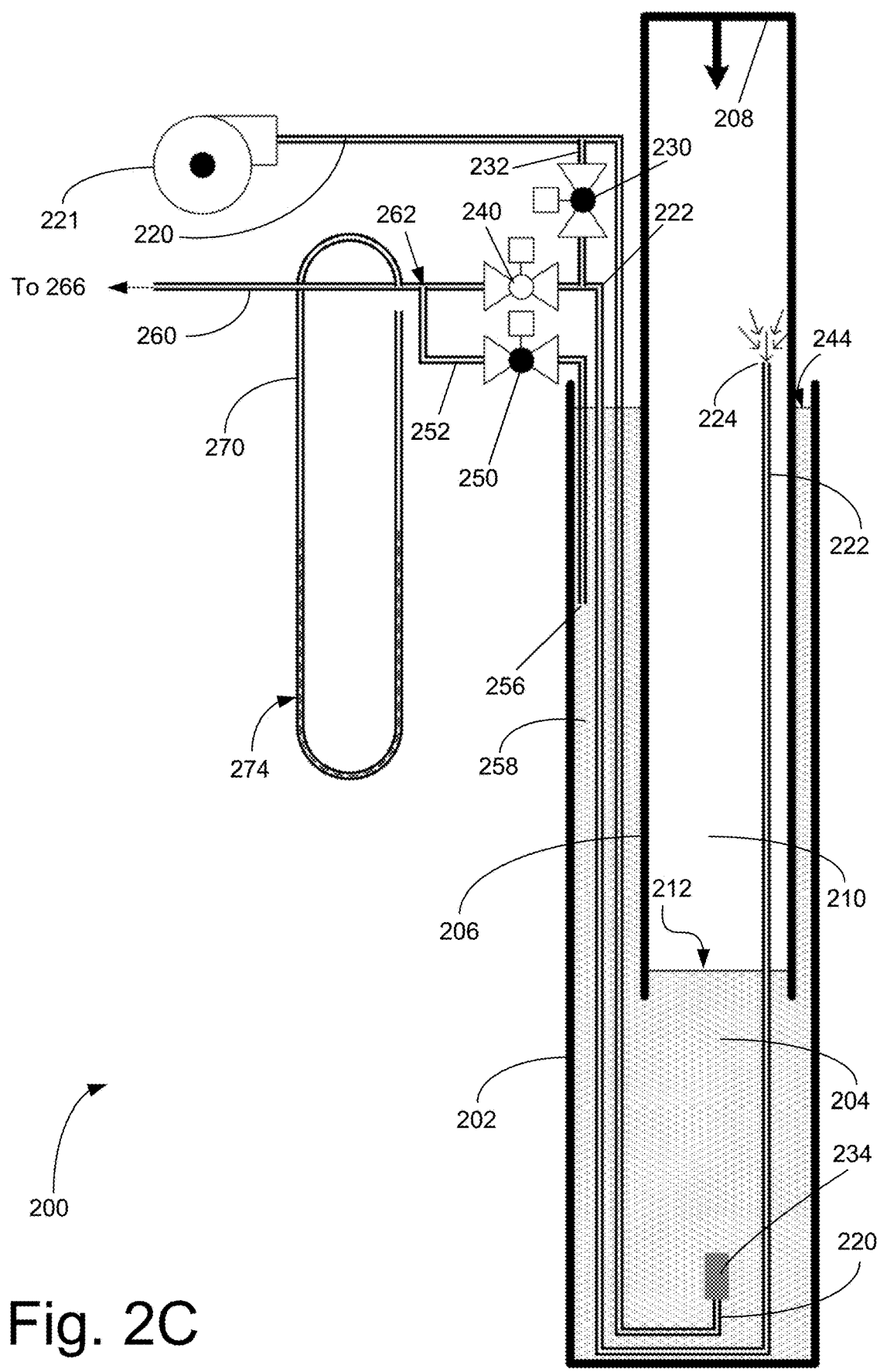

FIG. 2C shows the ICHV apparatus in the ready-to-deliver State 1. The inner cylinder 206 achieves its maximum height or elevation and the air source de-energizes (e.g., by turning off the air pump 221). For example, the maximum volume proximity sensor trips upon contact with the risen inverted cylinder 206 and signals the air pump 221 to turn off via the controller. The prescribed tidal volume is achieved as the closed top 208 of the inverted inner cylinder 206 (or the weight disposed on top) contacts the terminal of the maximum volume proximity sensor and completes the sensor circuit, signaling the gas supply flow to stop via the controller. The apparatus is ready to deliver the breathing gas to the patient.

When a breath is sensed as being demanded (on-demand breathing) or when a first preset timing or time limit is reached (mandatory breathing), the inhalation valve 240 separating the trapped breathing gas supply 210 from the patient opens, allowing the gas to escape directly to the patient. The exhalation valve 250 for the PEEP tube 252 closes at the same time. For example, if operated in the on-demand breathing mode as opposed to the mandatory breathing mode, the apparatus awaits a patient breath demand signal, which can be detected, for instance, by a breath demand pressure or vacuum sensor or an inhalation sensor (e.g., manometer 270) disposed between the inhalation valve 240 and the patient and sensing a pressure drop and generating a breath demand signal by the inhalation sensor. The apparatus may sense a partial vacuum inhalation demand from the patient via the breath demand pressure sensor, the controller opens the inhalation valve 240, and gas escapes from the gas volume inside the inverted cylinder space or chamber 210 of the inverted cylinder 206 via the patient supply or inhalation tube 222. The inverted cylinder 206 sinks at constant pressure and velocity due to gravity.

In the on-demand breathing operation, the patient breath demand signal is used to open the inhalation valve 240. Alternatively, in a mandatory breathing operation, the controller opens the inhalation valve 240 to allow a preset amount of inhalation time for inhalation and closes the inhalation valve 240 to allow a preset amount of exhalation time for exhalation at preset timings.

Figure 2D:
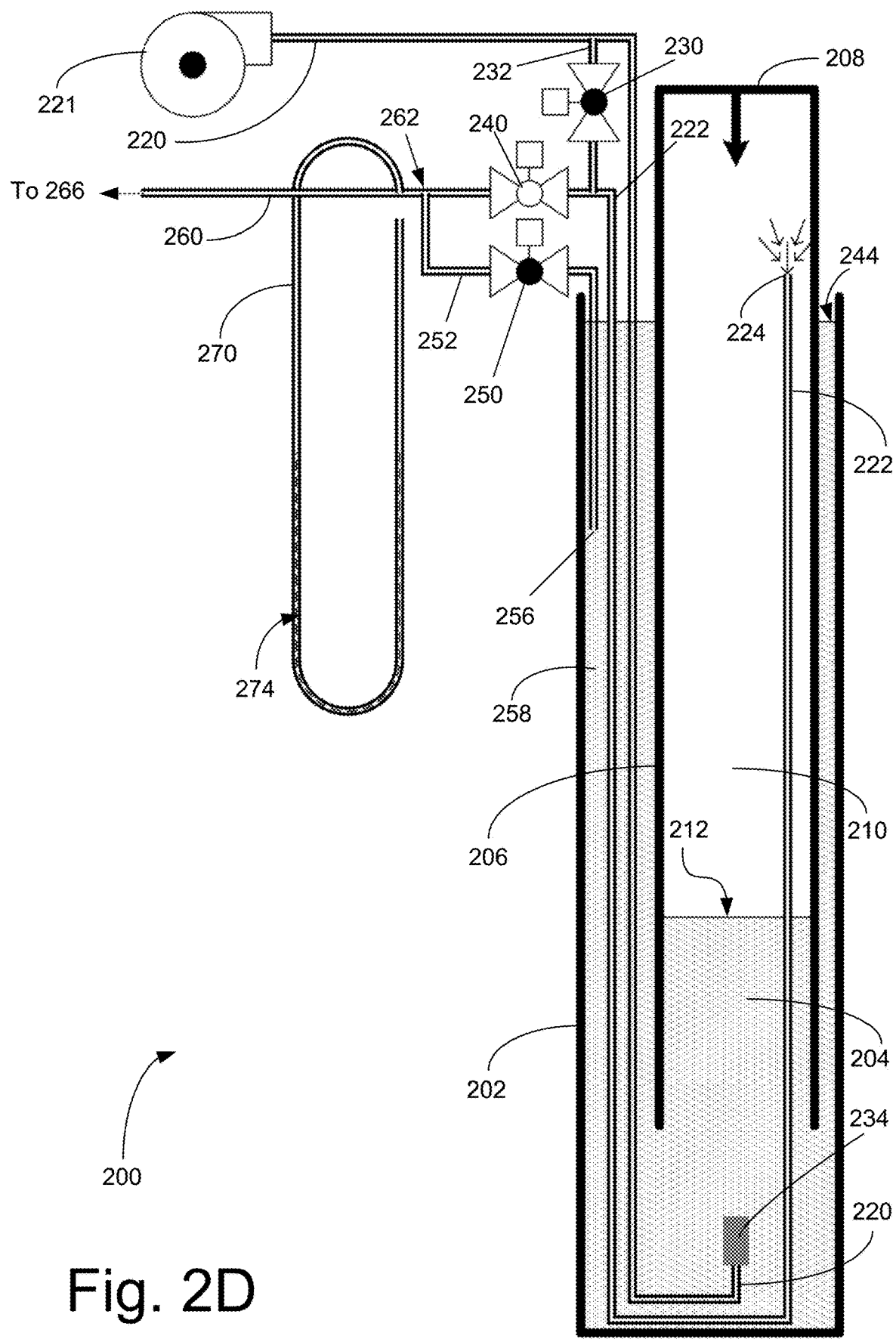

FIG. 2D shows the ICHV apparatus in a breath-delivery process from State 1 to a breath-delivered State 2. The inner cylinder 206 continues to sink lower at constant velocity due to gravity as gas is conveyed to the patient at the pressure indicated by the vertical disparity between the water bath's lower free surface 212 within the inner cylinder 206 and upper free surface 244 of the outer cylinder 202. The breathing gas delivery flow rate is determined mostly by the breathing tube diameter of the inhalation line 222 (and of the patient breathing line 260 beyond the junction 262) and the pressure drop through the inhalation valve 240. When the inner cylinder 206 reaches its minimum height, the process recycles.

Figure 2E:
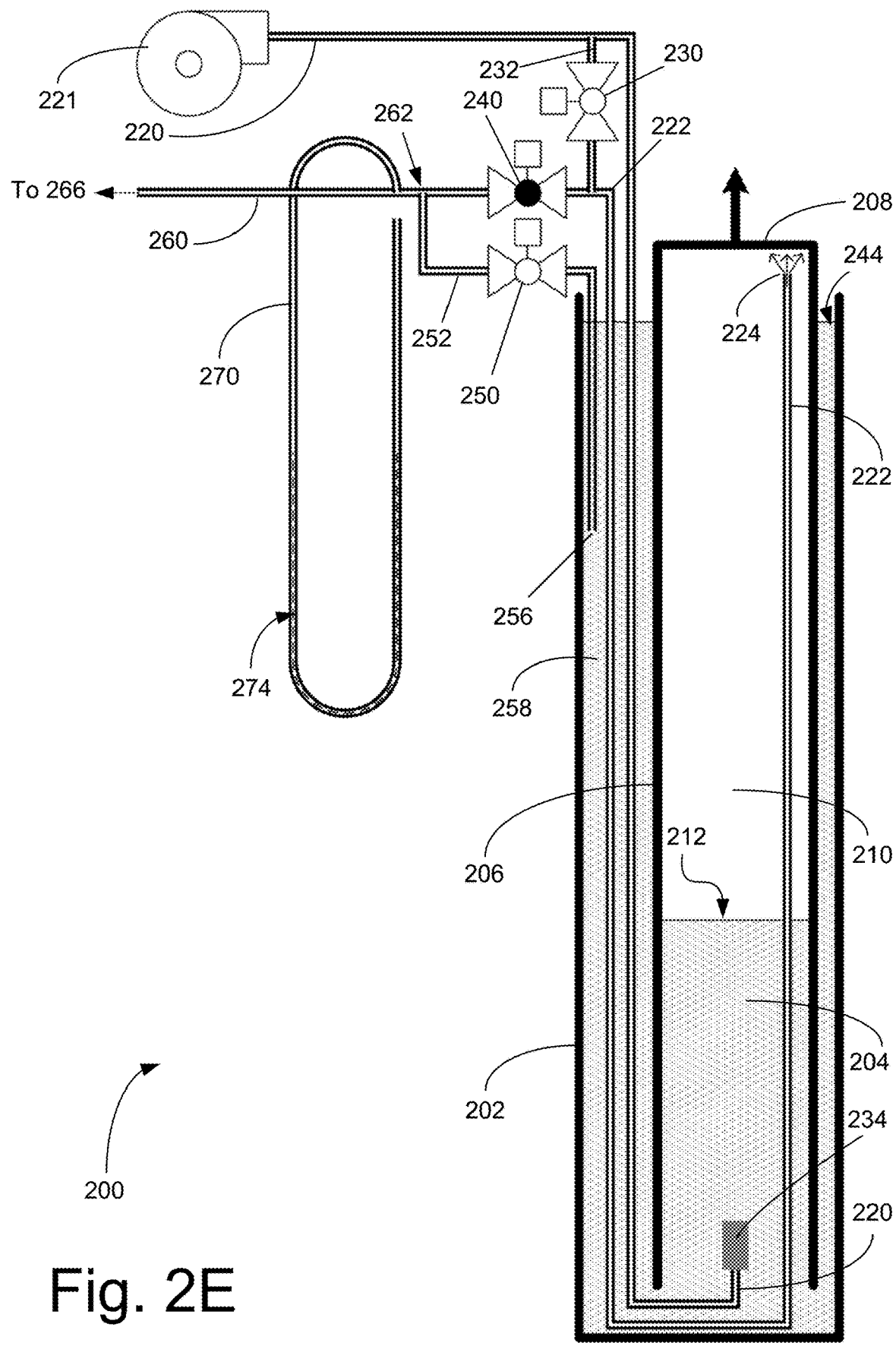

FIG. 2E shows the ICHV apparatus in the breath-delivered State 2 ready for charging in the non-conditioning mode (as opposed to charging in the bubble-conditioning mode of FIG. 2B). The inverted cylinder 206 has sunken to the minimum elevation, delivering a prescribed amount of breathing gas (tidal volume) from the gas volume of the inverted cylinder space 210 to the patient. For example, the minimum volume proximity sensor, when activated, signals the controller to close the inhalation valve and open the exhalation valve. The exhalation backpressure (i.e., the PEEP) is hydrostatically provided via the water in the cylindrical bucket or container 202 and strategic placement of the exhalation outlet port 256 of the exhalation line 252 in the water column or bath 204, as discussed above. The exhalation line 252 is opened to permit an exhalation gas flow from the patient through the exhalation inlet to the exhalation outlet 256 disposed in the liquid between the inverted container wall and the outer container wall.

The inner cylinder 206 is sensed to be at the preset minimum height. When running in non-conditioning mode, the breathing gas supply source, an air pump 221 in this case, energizes and delivers air via the bubbler bypass valve 230 in an open position with most of the gas arriving via the tube 222 terminating at the inhalation inlet (which now serves as the non-conditioning gas supply outlet 224) disposed inside the inner cylinder in the inverted cylinder space 210 above the water bath's free surface 212, causing the inner cylinder 206 to begin to rise. The inhalation valve 240 is closed. The tube 222 serves as an inhalation line with gas flowing out of the inverted cylinder space 210 and, in the non-conditioning mode, a gas supply line with gas flowing into the inverted cylinder space 210. Meanwhile, the patient is free to exhale into the water bath via the exhalation line 252 with the exhalation outlet end 256 terminating at the preset depth based on the prescribed positive end-expiratory pressure (PEEP).

Figure 2F:
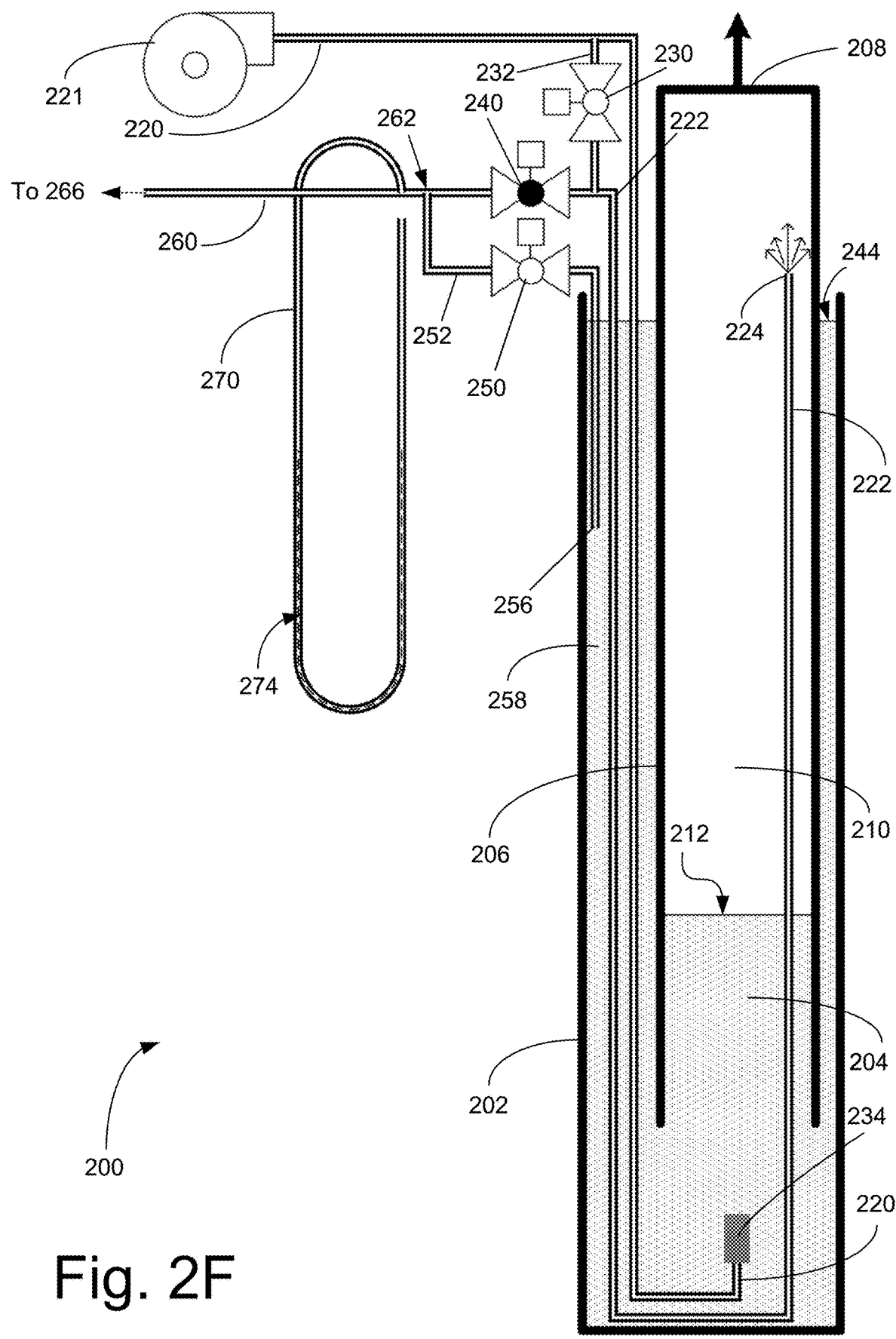

FIG. 2F shows the ICHV apparatus in a charging-and-expiration process from State 2 to State 1 in the non-conditioning mode. The air pump 221 continues to deliver air via the bubbler bypass valve 240 until the inner cylinder 206 has risen again at the constant pressure to the preset height based on the prescribed tidal volume to be delivered. The patient is still free to exhale into the water bath 204 via the exhalation line 252 with the exhalation outlet 256 terminating at the preset depth based on the prescribed PEEP. The patient exhales via the exhalation line 252 against the hydrostatic pressure prescribed by the PEEP tube terminal depth of the exhalation outlet 256 submerged in the water bath 204. The exhalation bubbles rise in the annular space 258 around the inverted inner cylinder 206. Humidity in the exhaled breath is reabsorbed into the water bath 204. The gas supply 221 flows breathing gas to the inverted cylinder space 210. The breathing gas causes the inverted cylinder 206 to rise at constant pressure again. The inner cylinder 206 charges during expiratory gesture.

Figure 2G:
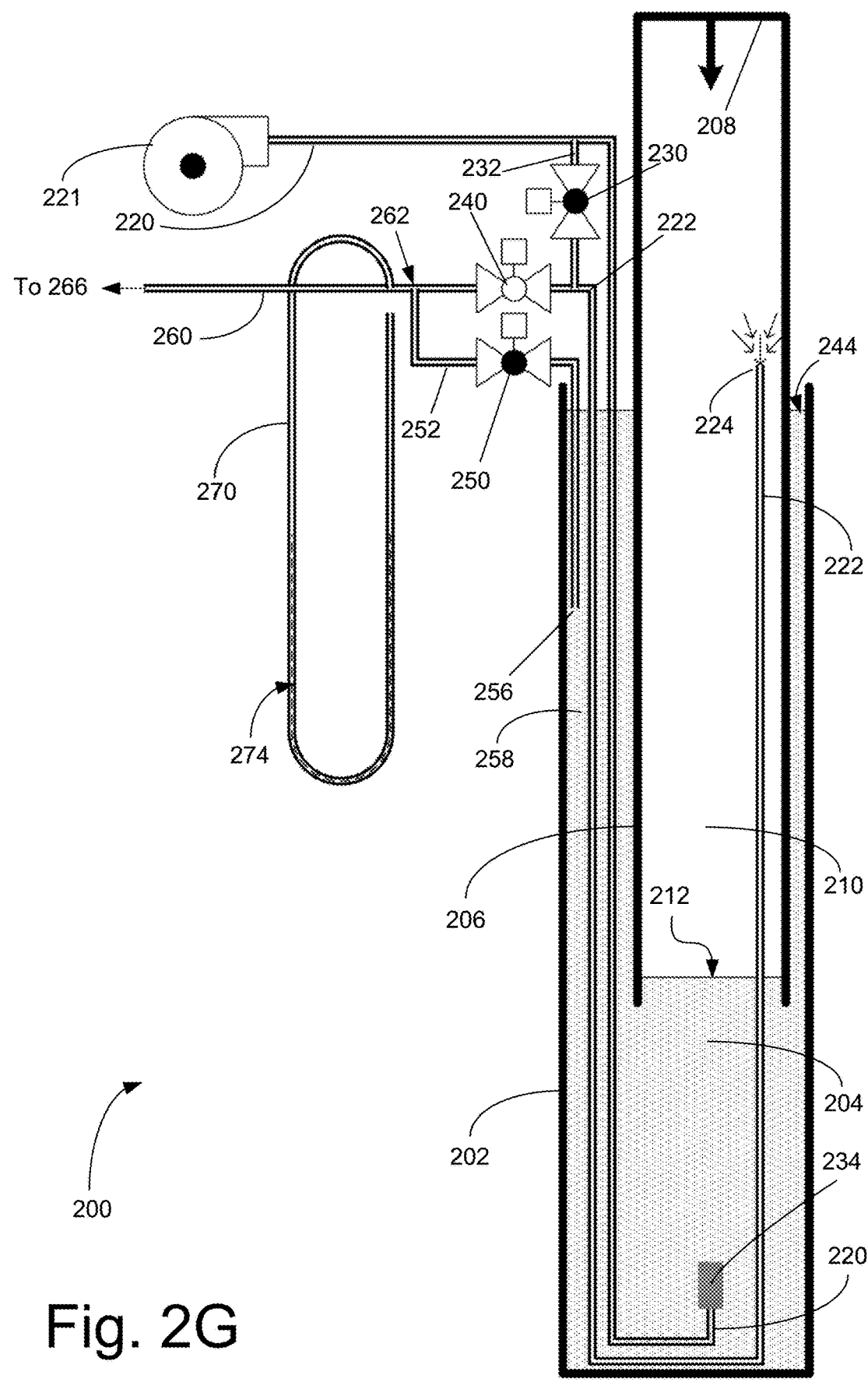

FIG. 2G shows the ICHV apparatus in the ready-to-deliver State 1. The inner cylinder 206 again achieves its maximum height and the air source 221 de-energizes. The inner cylinder 206 again (similar to FIG. 2C) achieves its maximum height or elevation and the air source de-energizes (e.g., by turning off the air pump 221). Tidal volume is added and then breathing gas delivery to the patient is ready to begin as the patient concludes the expiratory gesture. When a breath is sensed as being demanded (on-demand breathing) or a second preset timing or time limit is reached (mandatory breathing), the inhalation valve 240 separating the trapped breathing gas supply 210 from the patient opens, allowing the gas to escape directly to the patient. The exhalation valve 250 for the PEEP tube 252 closes at the same time.

Figure 2H:
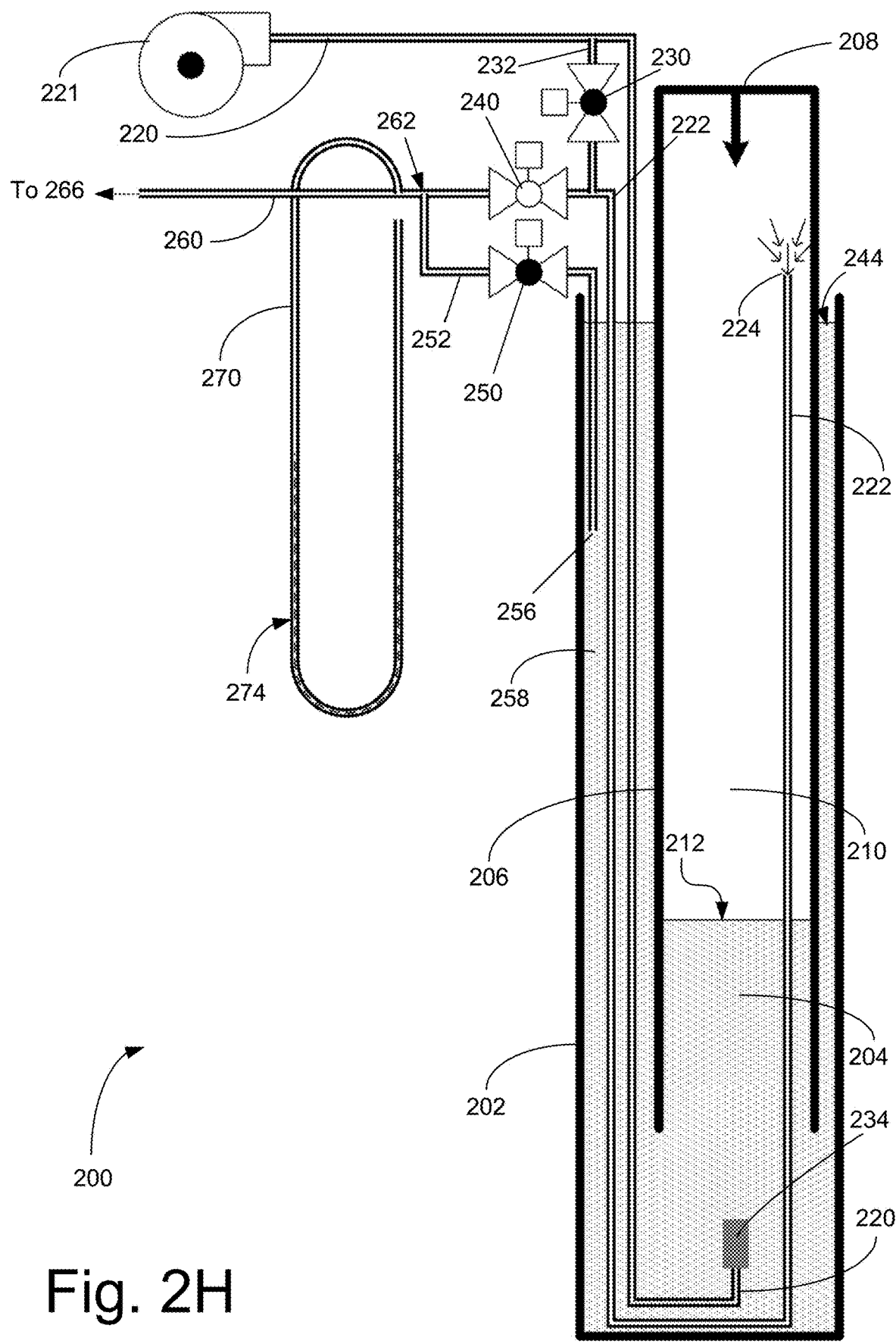

FIG. 2H shows the ICHV apparatus in a breath-delivery process from State 1 to State 2. Similar to FIG. 2D, the inner cylinder 206 continues to sink lower as gas is conveyed to the patient at the pressure indicated by the vertical disparity between the water bath's lower free surface 212 within the inner cylinder 206 and upper free surface 244 of the outer cylinder 202. When the inner cylinder 206 reaches its minimum height, the process recycles.

FIG. 3A shows an example of a breath demand mode water switch for switching on and off of the inhalation valve 240 in the patient breathing line 260 for on-demand breathing instead of mandatory breathing. It uses a non-toxic electrolytic liquid (e.g., saltwater) 314 in a manometer 310 connected to the patient breathing line 260 (or the inhalation tube or patient supply tube 222 if the exhalation line 252 is completely separate from the inhalation line 222 without merging) to complete the circuit of an electrical sensor (with sensor line 330 and sensing wire 340 as described below) when a patient begins to inhale. The manometer 310 is disposed between the inhalation valve 240 and the inhalation outlet 266 connected to the patient. The (small) partial vacuum caused by the initial inspiratory gesture closes the circuit between the energized terminal and sensor terminal, which tells the microcontroller to open the inhalation valve 240 to pressurize the patient breathing line 260 with breathing gas. The switch is reliable and easy to fabricate. It also provides secondary protection against over-pressurization of the patient breathing line 260 by setting the manometer open end 320 at some prescribed height.

In the neutral state as illustrated in FIG. 3A, an insulated sensing wire 340 terminates with an electrically uninsulated terminal 342 slightly above the free surface of an electrolytic solution 314 trapped in the U-manometer 310. Another wire, sensor line 330 at a defined reference voltage, terminates with its electrically uninsulated end 332 submerged in the solution 314. The electrical circuit is broken as long as the electrolytic solution 314 is not in contact with both terminals 332, 342 simultaneously. The inspiratory valve 240 separating the patient from the trapped breathing gas supply 210 is closed. The normally grounded sensor line 330 communicates with the inhalation valve 240 via the microcontroller and relay. When no breath is demanded, the circuit is broken and the demand signal is negative (LOW). The sensor line 330 extends from the inhalation valve 240 to the electrically uninsulated end 332 at the bottom of the electrolytic solution manometer tubing 310. A low-voltage (e.g., 5 VDC) signal source is coupled to the sensing wire 340 which terminates with the electrically uninsulated terminal 342 just above the electrolytic solution free surface when the system is in the neutral position. The live end 342 of the circuit is exposed but not in contact with the electrolytic solution when no breath is demanded. The height of the open end 320 of the electrolytic solution tube 310 provides a secondary safety feature preventing overpressure delivery.

In the active state as illustrated in FIG. 3B, the sensor line 330 communicates with the inhalation valve 240 via the microcontroller and relay. When a slight drop in pressure occurs due to the onset of a breath demand by an inhaling patient, the solution 314 within the manometer 310 shifts toward the exposed sensing wire's bare terminal 342 and the breath demand signal is positive (HIGH). A momentary suction subsides when the inhalation valve 240 opens and pressurizes the breathing line 260 to the patient. The live end 342 of the circuit is now exposed to the electrolytic solution 314 when a breath is demanded causing a partial vacuum 350 in the manometer 310, causing the liquid 314 to migrate upward via the partial vacuum 350. When the solution 314 rises enough to submerge both terminals 332, 342, the electrical circuit is completed and the controller senses a demand signal. The controller responds by opening the inspiratory valve 240 and closing the expiratory (PEEP) valve (250 in FIGS. 3A-3H).

ICHV Process

Figure 4:
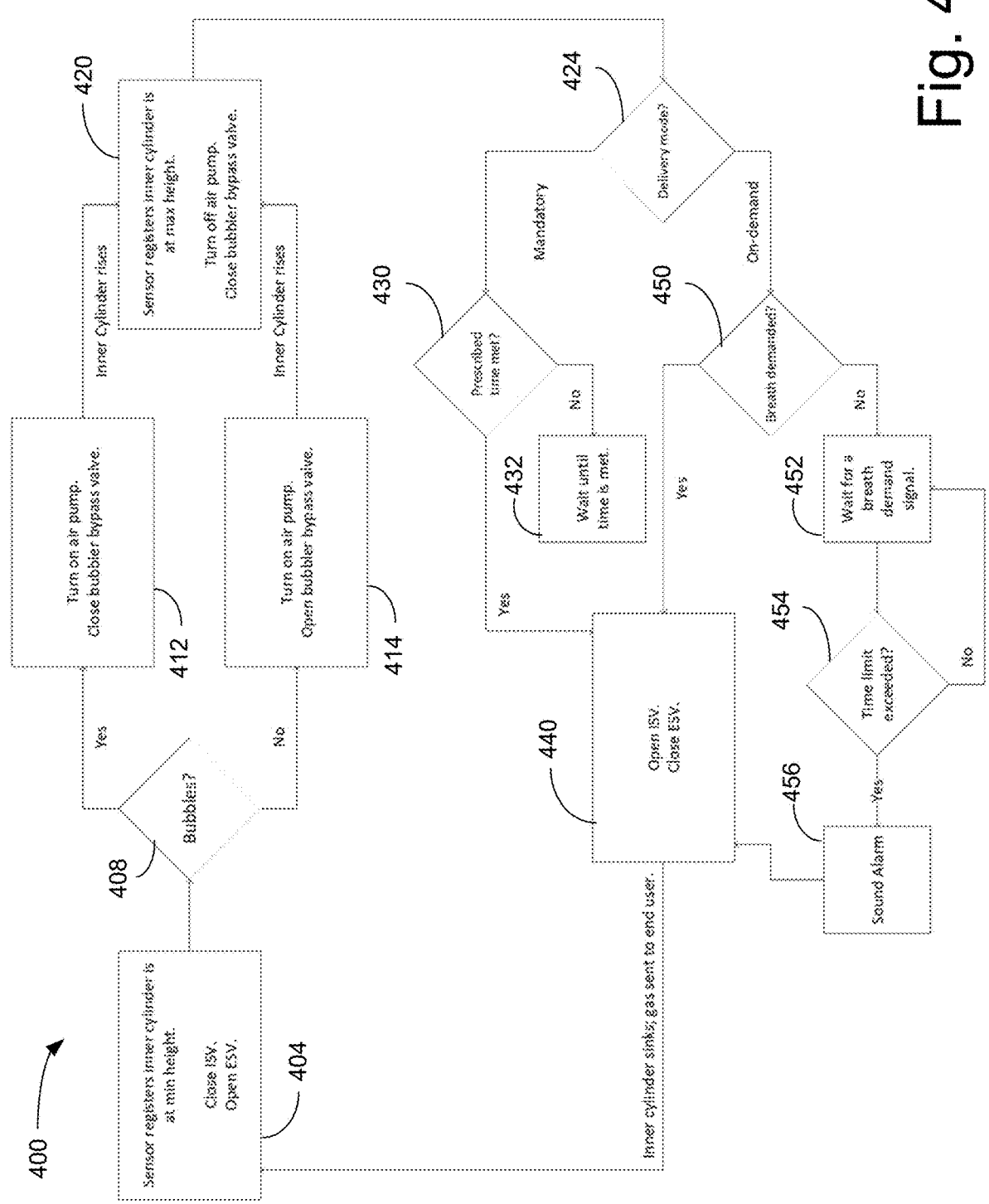
FIG. 4 is a flow diagram summarizing the process of operating the ICHV apparatus of FIGS. 2A-2H.

FIG. 4 is a flow diagram summarizing the process 400 of operating the ICHV apparatus of FIGS. 2A-2H. The apparatus is in the startup state shown in FIG. 2A and described above. The minimum elevation sensor registers that the inner cylinder 206 is at the minimum elevation. In the preparation step 404 prior to charging, the inhalation valve 240 is closed and the exhalation valve 250 is opened. Next, the user or operator specifies (manually or via the controller) whether charging will include bubbles (step 408). If bubbles are included in the bubble-conditioning mode, the charging step 412 closes the bubbler bypass valve 230 and starts the air pump 221. The breathing gas supply flow is directed into the gas volume of the inverted cylinder space 210 via the bubbler 234 to achieve the target hydrostatic delivery pressure in the gas volume and lift the elevation of the inner cylinder 206. If bubbles are not included in the non-conditioning mode, the charging step 414 opens the bubbler bypass valve 230 and starts the air pump 221 to direct breathing gas into the gas volume of the inverted cylinder space 210 via the non-conditioning gas supply line 222.

In ready-to-deliver step 420, upon detection that the inner cylinder 206 has reached a preset maximum elevation (e.g., by the maximum volume proximity sensor or maximum elevation sensor), the breathing gas supply flow into the gas volume is closed (e.g., by deenergizing the air pump 221). If the bubbler bypass valve 230 was opened (in the non-conditioning mode), it is now closed. Next the operator specifies (manually or via the controller) whether the delivery mode is mandatory or on-demand (step 424).

For mandatory delivery, the next step 430 is to determine whether the first prescribed or preset timing has been reached. If not, the system waits until the first preset timing is reached (step 432). When the first preset timing is reached, a breath-delivery step 440 opens the inhalation line 222 (e.g., by opening the inhalation valve 240) to flow breathing gas from the gas volume in the inverted cylinder space 210 to the patient at the target hydrostatic delivery pressure, lowering the elevation of the inner cylinder 206 due to lost buoyancy resulting in sinkage. The exhalation valve 250 for the PEEP tube 252 closes at the same time.

For on-demand delivery, the next step 450 is to determine whether there is patient breath demand. Upon detection of a patient breath demand signal, for instance, by a breath demand pressure or vacuum sensor (e.g., manometer 270), the breath-delivery step 440 opens the inhalation line 222 to flow breathing gas to the patient and closing the exhalation valve 250.

The process returns to step 404, which is now a charging-and-expiration step, upon detection that the inner cylinder has reached a preset minimum elevation (breath delivered, e.g., by the minimum volume proximity sensor). The inhalation valve 240 is closed and the exhalation valve 250 is opened.

ICHV Apparatus—Additional Features and Other Embodiments

Figure 5:
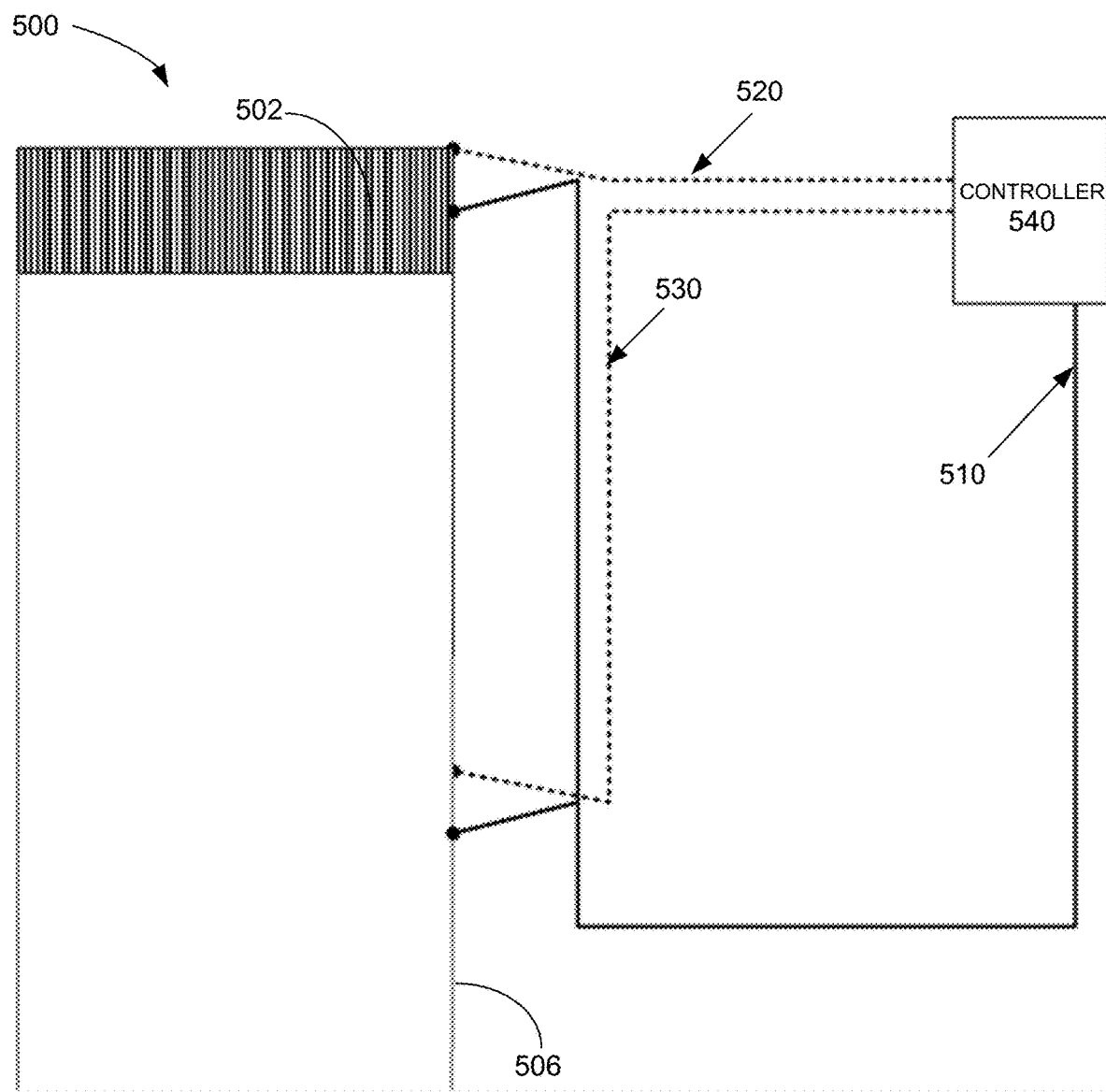
FIG. 5 is a schematic view illustrating an example of proximity sensors in an ICHV apparatus.

FIG. 5 is a schematic view illustrating an example of proximity sensors in an ICHV apparatus. The proximity sensors 500 include a conductive layer 502 attached to the closed top of the inverted inner cylinder 506 (e.g., by adhesion). A reference voltage line 510 is disposed at an upper elevation and a lower elevation. An upper sensing wire 520 is disposed at the upper elevation (which represents the maximum volume proximity) and a lower sensing wire 530 is disposed at the lower elevation (which represents the minimum volume proximity). The reference voltage line 510, upper sensing wire 520 and the lower sensing wire 530 are connected to a controller 540.

The maximum volume proximity sensor or maximum elevation sensor is formed by an exposed disconnected terminal of the reference voltage line 510 and an exposed disconnected terminal of the upper sensing wire 520 at the upper elevation. When the conductive layer 502 attached to the inner cylinder 506 simultaneously contacts both terminals, the upper sensing wire 520 adopts the reference voltage and the controller 540 sense the cylinder's location at the maximum volume proximity level.

The minimum volume proximity sensor or minimum elevation sensor is formed by an exposed disconnected terminal of the reference voltage line 510 and an exposed disconnected terminal of the lower sensing wire 530 at the lower elevation. When the conductive layer 502 attached to the inner cylinder 506 simultaneously contacts both terminals, the lower sensing wire 530 adopts the reference voltage and the controller 540 senses the cylinder's location at the minimum volume proximity level.

Figure 6:
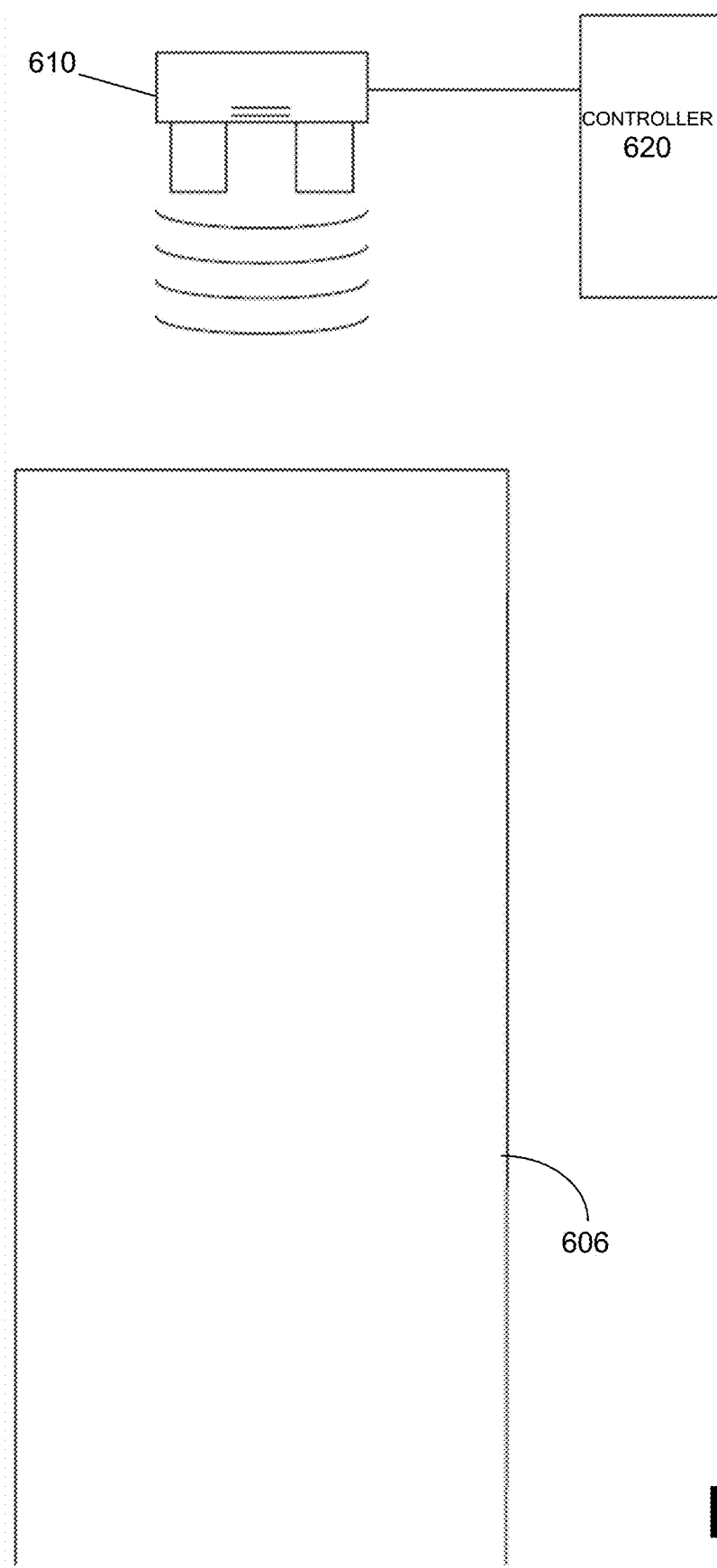
FIG. 6 is a schematic view illustrating another example of a proximity sensor in an ICHV apparatus.

FIG. 6 is a schematic view illustrating another example of a proximity sensor in an ICHV apparatus. An ultrasonic ranging sensor 610 is positioned directly above and pointed toward the closed top of the inverted inner cylinder 606 to serve as the proximity sensor. The ultrasonic sensor 610 is coupled to a controller 620. Other embodiments include magnetic reed switches or an optical ranging sensor positioned directly above and pointed toward the closed top of the inner cylinder 606.

Figure 7:
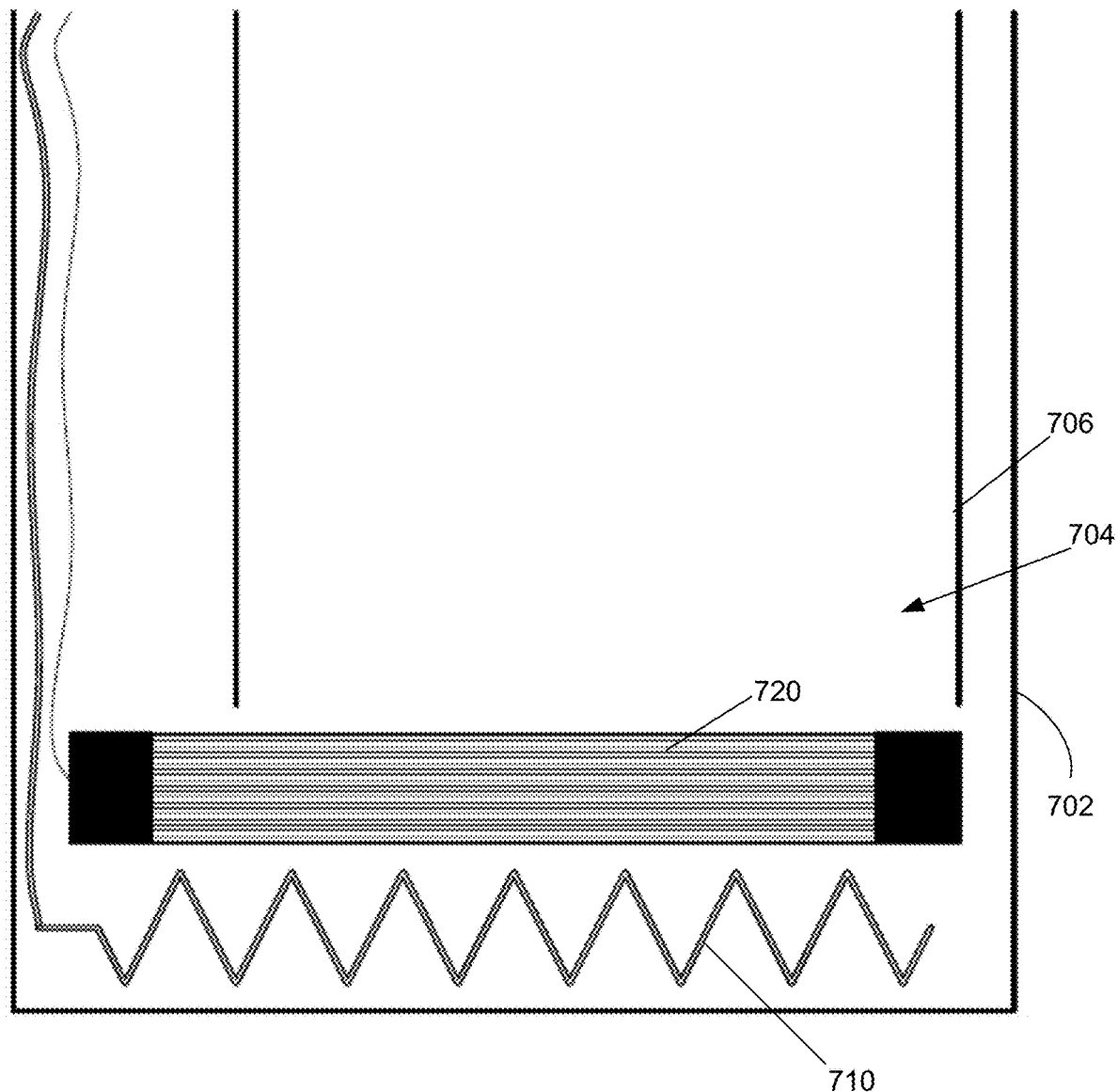
FIG. 7 is a schematic view illustrating an example of a heater and a UV light in an ICHV apparatus.

FIG. 7 is a schematic view illustrating an example of a heater and a UV light in an ICHV apparatus. A heating element 710 such as a thermostatic heater or an electric resistance heater is provided inside the outer upright cylinder 702, to heat the water bath 704 in which the inner inverted cylinder 706 is partially submerged, to compensate for the absence of biologically available heating via sinus cavities. An ultraviolet (UV) light 720 is provided inside the upright cylinder 702 to perform virus decontamination and prevent algal and bacterial growth. In other embodiments, the heating element and/or UV light may be disposed outside the water bath 704. In some embodiments, the UV light kills pathogens; alternatively, increased salinity in the water bath can be used.

Figure 8:
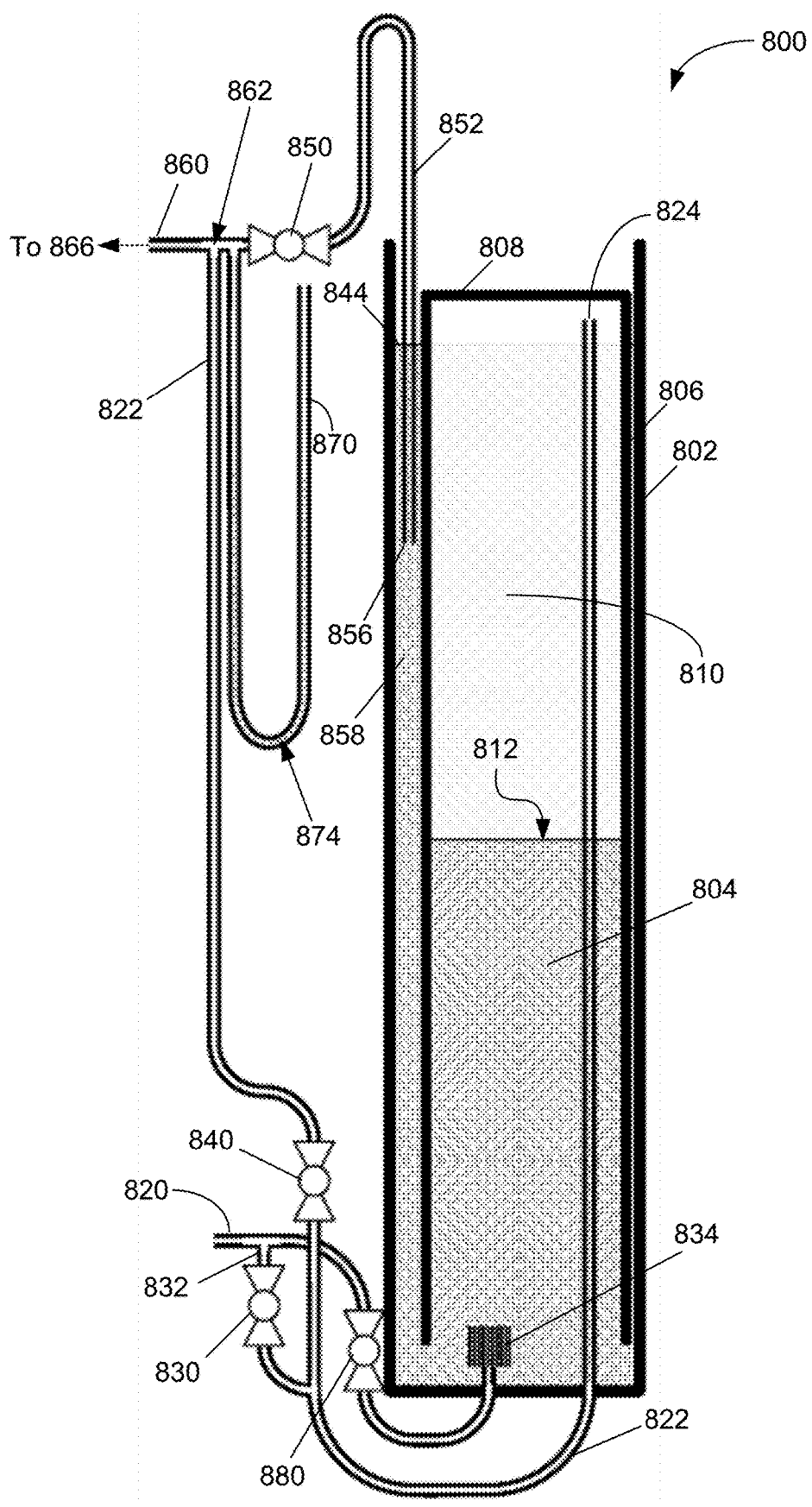
FIG. 8 schematically illustrates an ICHV apparatus according to another embodiment.

FIG. 8 schematically illustrates an ICHV apparatus according to another embodiment. The ICHV apparatus 800 is similar to the ICHV apparatus 200 of FIGS. 2A-2H, including the following similar components: an upright outer cylinder 802 containing a water bath 804, an inverted inner cylinder 806 having a closed top 808, a gas volume in an inverted cylinder space 810 trapped by the water bath 804 in the upright cylinder 802 above an inverted inner cylinder free water surface 812, a gas supply line or tube 820, a bubbler bypass valve (one-way) 830 provided on a bubbler bypass line or tube 832, a bubbler 834, an inhalation or inspiratory valve or patient gas delivery valve (one-way) 840 provided on a patient supply (or patient gas delivery) or inhalation line or tube 822 to supply breathing gas, an exhalation or expiratory valve (one-way) 850 provided on an exhalation line or tube 852 to permit exhaled breath of the patient to flow, in an opened position, from an exhalation inlet coupled to the patient (e.g., via a mask) to an exhalation outlet 856 in the water bath 804 of the upright cylinder 802, an annular region 858 between the upright cylinder 802 and the inverted cylinder 806. The inhalation line 822 and the exhalation line 852 merge at a junction 862 into a single patient breathing line 860 coupled to the patient. Disposed between the junction 862 and the exhalation valve 850 is a manometer 870 containing a non-toxic electrolytic liquid 874. The single patient breathing line 260 leads to a breathing line opening 866 coupled to the patient, which is the inhalation outlet during inhalation by the patient and the exhalation inlet during exhalation by the patient. The inner cylinder's free surface 812 will always be lower than the outer cylinder's free surface 844 (the height difference corresponds to the hydrostatic delivery pressure).

The main difference between the ICHV apparatus 200 of FIGS. 2A-2H and the ICHV apparatus 800 of FIG. 8 is the presence of a gas supply valve 880 in the gas supply line 820 and the absence of the air pump 221 in the ICHV apparatus 800. As such, instead of controlling the gas supply flow by controlling the air pump 221 in the ICHV apparatus 200, the ICHV apparatus 800 controls the gas supply flow by controlling the gas supply valve 880, which may also be a solenoid valve. Other than this specific feature, the operation of the ICHV apparatus 800 is substantially identical to the operation of the ICHV apparatus 200.

Figure 9:
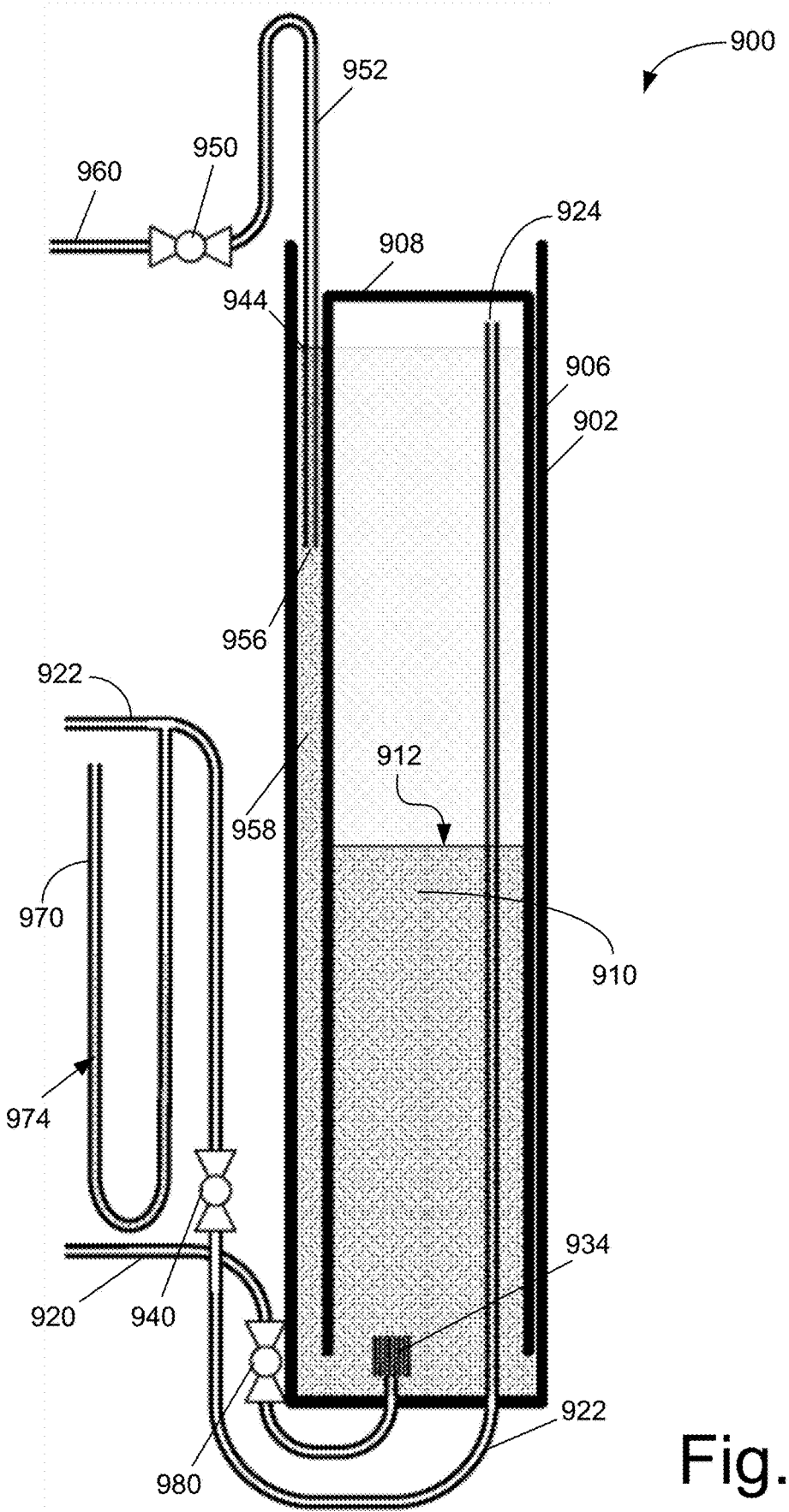
FIG. 9 schematically illustrates an ICHV apparatus according to another embodiment.

FIG. 9 schematically illustrates an ICHV apparatus according to another embodiment. The ICHV apparatus 900 has many features that are similar to those in the ICHV apparatus 800 of FIG. 8, including the following similar components: an upright outer cylinder 902 containing a water bath 904, an inverted inner cylinder 906 having a closed top 908, a gas volume in an inverted cylinder space 910 trapped by the water bath 904 in the upright cylinder 902 above an inverted inner cylinder free water surface 912, a gas supply line or tube 920 leading to a bubbler 934 disposed in the water bath 904, a gas supply valve (one-way) 980 provided on the gas supply line 920, an inhalation or inspiratory valve or patient gas delivery valve (one-way) 940 provided on a patient supply (or patient gas delivery) or inhalation line or tube 922 to supply breathing gas, an exhalation or expiratory valve (one-way) 950 provided on an exhalation line or tube 952 to permit exhaled breath of the patient to flow, in an opened position, from an exhalation inlet coupled to the patient (e.g., via a mask) to an exhalation outlet 956 in the water bath 904 of the upright cylinder 902, an annular region 958 between the outer container wall of the upright cylinder 902 and the inner container wall of the inverted cylinder 906. Disposed in the inhalation line 922 downstream of the inhalation valve 940 (between the inhalation valve 940 and the patient) is a manometer 970 containing a non-toxic electrolytic liquid 974. The inner cylinder's free surface 912 will always be lower than the outer cylinder's free surface 944 (the height difference corresponds to the hydrostatic delivery pressure).

The main difference between the ICHV apparatus 900 of FIG. 9 and the ICHV apparatus 800 of FIG. 8 is that the inhalation line 922 and the exhalation line 952 do not merge into a single patient breathing line coupled to the patient but remain separate and are separately coupled to the patient. Furthermore, the ICHV apparatus 900 does not include a bubbler bypass valve 830 provided on a bubbler bypass line 832 as provided in the ICHV apparatus 800.

The operation of the ICHV apparatus 900 is substantially identical to the operation of the ICHV apparatus 800. It is simpler because the ICHV 900 does not have to operate the absent bubbler bypass valve 830 in the bubbler bypass line 832 of the ICHV apparatus 800. The opening and closing of the inhalation valve 940 in the inhalation line 922 and the exhalation valve 950 in the exhalation line 952 are similar to the opening and closing of the inhalation valve 840 in the inhalation line 822 and the exhalation valve 850 in the exhalation line 852. Because the inhalation line 922 and the exhalation line 952 do not merge into a single patient breathing line (in which there is two-way air flow), there may be less restrictions or requirements on the operation of the inhalation valve 940 and the exhalation valve 950 and coordination of the operation in the separate inhalation line 922 and exhalation line 952 (in which there is one-way air flow in each). This separation of flows also avoids "dead air" residing and oscillating in the tubing between the ICHV and patient. In a single tube design, the potential exists for residual quantities of exhaled gas from a previous breath to remain in the tube only to be fed back to the patient in the initial stage of new breath delivery.

Figure 10:
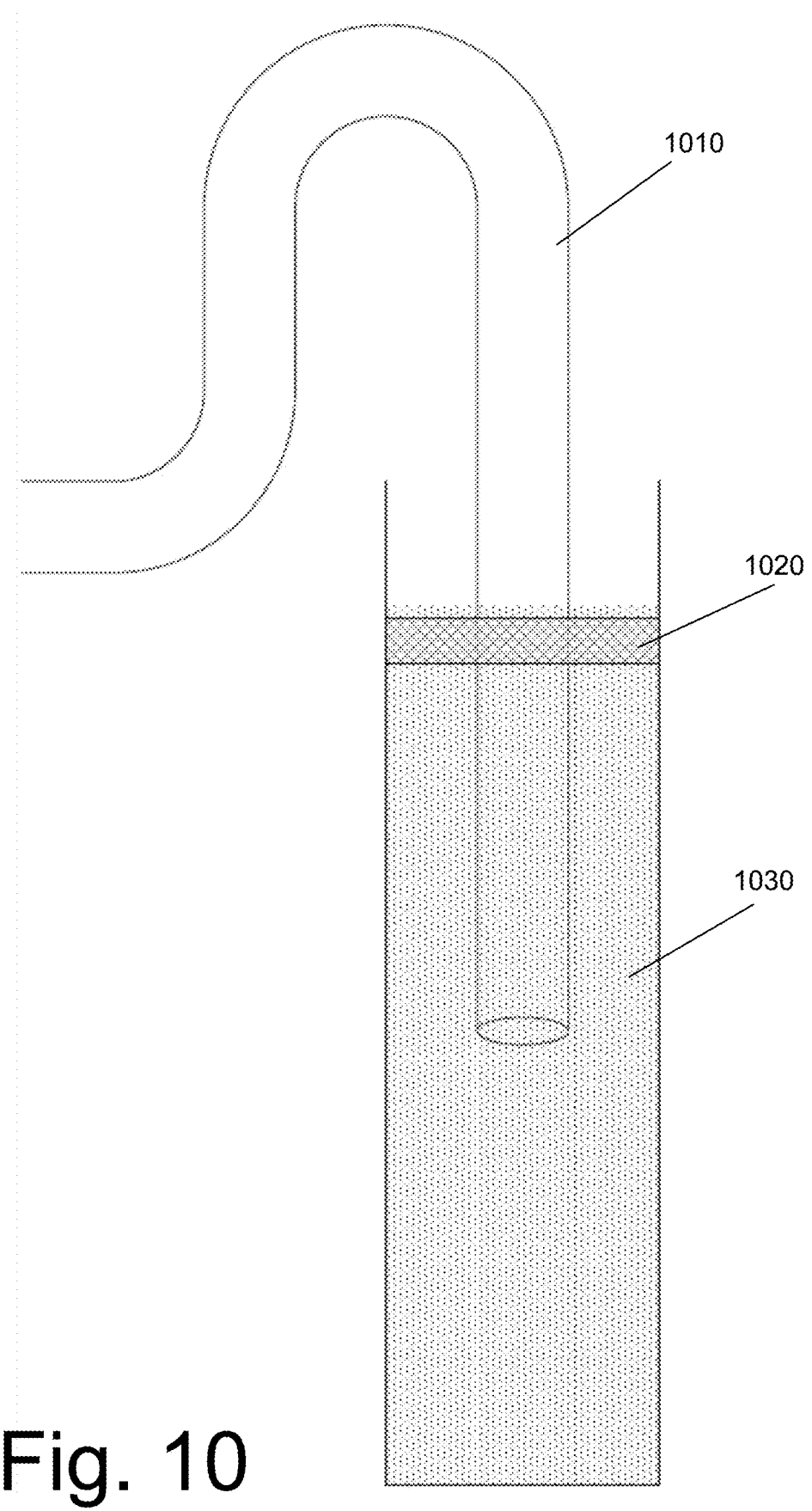
FIG. 10 shows an example of a PEEP tube terminating in its own separate sterilization reservoir with permeable membrane shown near the top of the free surface.

FIG. 10 shows an example of an evaporation and humidification inhibitor for a PEEP tube 1010. If long-term use of the non-conditioning mode is intended, a thin layer of non-toxic oil with low volatility and specific gravity less than one, such as partially-hydrogenated vegetable oil or food-grade mineral oil, may be employed as an evaporation and humidification inhibitor 1020 over a water reservoir. The oil blanket can be located on the water free surface (212 in FIG. 2A) within the inner cylinder (to minimize humidification), the water free surface of (244 in FIG. 2A) the outer cylinder (to minimize evaporation to the ambient environment), or both free surfaces. The PEEP tube 1010 terminates in its own separate sterilization reservoir with permeable membrane shown near the top of the free surface or a hydraulically separate PEEP reservoir to reduce PEEP variability during operation and to possibly aid in exhaled air sterilization.

Figure 11:
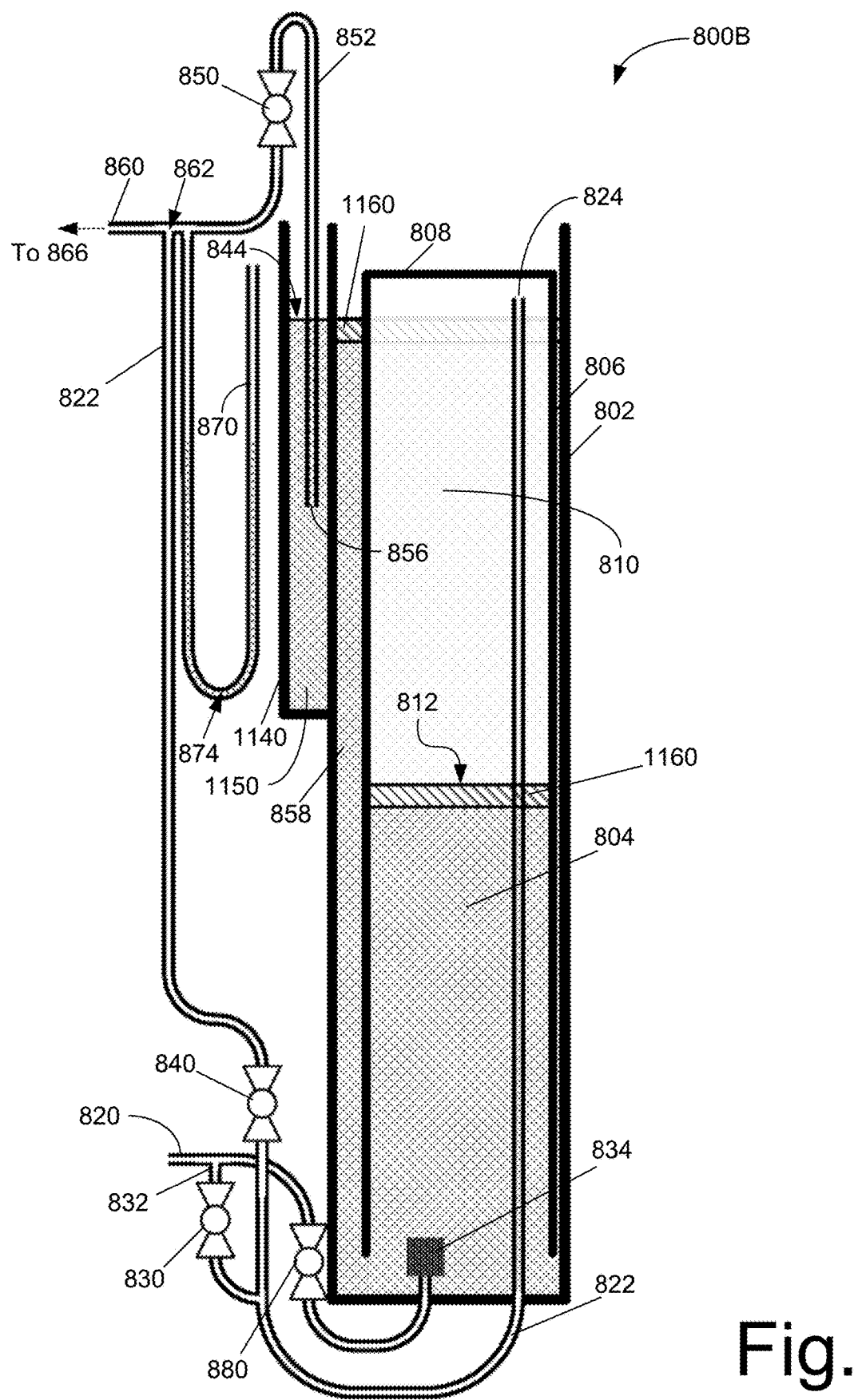
FIG. 11 is a modified version of the ICHV apparatus of FIG. 8 showing an example of a smaller reservoir of water treated with a sterilizing agent, hydraulically separated from the main water bath, for housing the reentrant PEEP tube terminus.

FIG. 11 shows an example of a smaller reservoir 1140 of water 1150 treated with a sterilizing agent (dissolved biocidal chemical or UV-C irradiation, for example) located either outside or, space permitting, inside the outer cylinder 802, but hydraulically separated from the main water bath 804, for housing the reentrant PEEP tube terminus 856. A permeable membrane, such as woven cotton, located below the surface of this PEEP bath 1150 may help break apart the large exhalation bubbles, mitigating sterilization further by increasing residency time and gas surface area. Another advantage to this arrangement is a more-consistent water level reducing the PEEP value's operationally unintended variability during inner cylinder 806 movement; adjustability by the user is still maintained. An evaporation and humidification inhibitor 1160 (e.g., oil blanket) is located on the water free surface 812 within the inner cylinder (to minimize humidification) and the water free surface 844 of the outer cylinder (to minimize evaporation to the ambient environment). The ICHV apparatus 800B of FIG. 11 is a modified version of the ICHV apparatus 800 of FIG. 8 with like reference characters for like parts.

The apparatus may be thought of as having means for directing a breathing gas to the inverted container space, to move the inverted container upward from a preset minimum elevation position when the breathing gas in the inverted container space reaches a hydrostatic delivery pressure, to continue moving the inverted container upward at the hydrostatic delivery pressure while a volume of the inverted container space increases at the hydrostatic delivery pressure, to stop moving the inverted container upward when the inverted container reaches a preset maximum elevation position, and to move the inverted container upward at the hydrostatic delivery pressure when the inverted container drops from the preset maximum elevation position to the preset minimum elevation position. In one example, such means may include the gas supply line 220, air pump 221, bubbler bypass valve 230, and inhalation valve 240. The means may further include the manometer 310 (having the electrolytic liquid 314 and connected to the patient breathing line 260 or the inhalation line 222) and the sensing wire 340, and/or may further include proximity sensor 500, reference voltage line 510, and upper sensing wire 520, and/or may further include the ultrasonic ranging sensor 610, and/or may further include the controller 130, 540, and/or 620. In another example, the means may include the gas supply line 820, bubbler bypass valve 830, bubbler bypass line 832, and inhalation valve 840. The means may further include the manometer 870 and/or may further include the proximity sensor 500, reference voltage line 510, upper sensing wire 520, and lower sensing wire 530, and/or may further include the ultrasonic ranging sensor 610, and/or may further include the controller 130, 540, and/or 620. In another example, the means may include the gas supply line 920, inhalation valve 940, and gas supply valve 980. The means may further include the manometer 970, and/or may further include the proximity sensor 500, reference voltage line 510, upper sensing wire 520, and lower sensing wire 530, and/or may further include the ultrasonic ranging sensor 610, and/or may further include the controller 130, 540, and/or 620.

The apparatus may also be thought of as having means for directing an exhalation gas flow, when the inverted container has reached the preset minimum elevation position, to permit the exhalation gas flow from the patient through the exhalation inlet to the exhalation outlet disposed in the liquid between the inverted container wall and the outer container wall, and, based on one of (1) detection of the target hydrostatic backpressure at the exhalation outlet or (2) a second preset timing, to stop the exhalation gas flow from the exhalation inlet to the exhalation outlet in the liquid at the fixed elevation. In one example, such means may include the exhalation valve 250 or 850 or 950. The means may further include the proximity sensor 500, reference voltage line 510, and lower sensing wire 530, and/or may further include the ultrasonic ranging sensor 610, and/or may further include the controller 130, 540, and/or 620.

ICHV Apparatus Characteristics

The ICHV apparatus may have different configurations with different characteristics including available tidal volume, delivery pressure, operational mass, and various dimensions. The various components can be custom-made using a variety of materials and processes or commercially available, at different price ranges. The present invention can be implemented based on various operational needs and budget constraints.

If less pressure and/or tidal volume is needed, it can be easily modified to suit the providers' needs with regard to tidal volume and delivery pressure or even modularized via optional extensions to make it taller (taller=greater capacity for pressure and volume).

Figure 12:
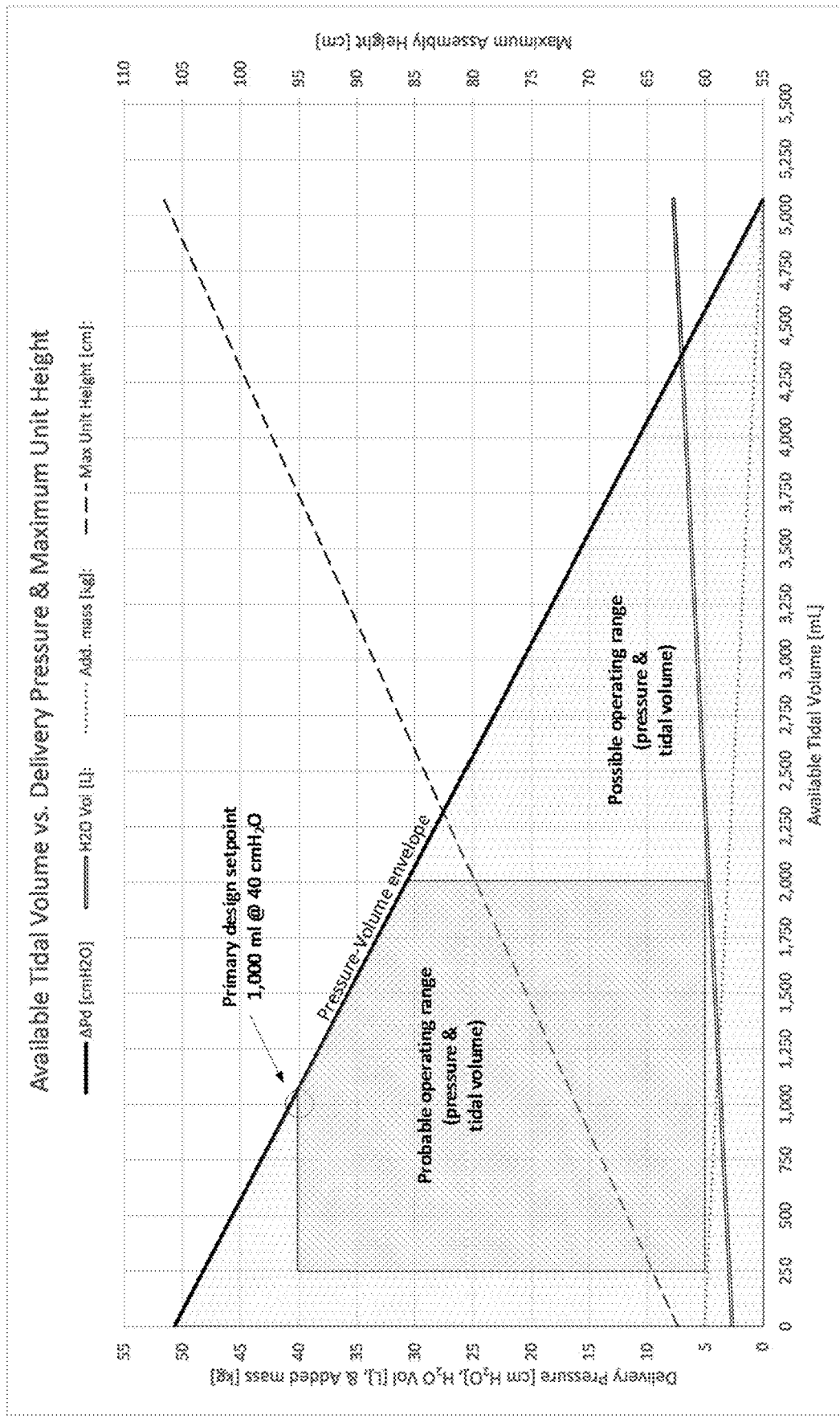
FIG. 12 shows a graph of available tidal volume, added mass, and maximum unit height versus delivery pressure of the ICHV apparatus of FIG. 8.

FIG. 12 shows a graph of available tidal volume, added mass, and maximum unit height versus delivery pressure of the baseline ICHV apparatus of FIG. 8. The added mass refers to the adjustable cylinder weights added to the inverted cylinder 606, for example, by placing them on top of the closed top 608 of the inverted cylinder 606. The dimensions of breadth-width-height (BWH) are as follows: $BWH_{min}$ of 12.4 cm×12.4 cm×57.9 cm (shipping dimension) and $BWH_{max}$ of 12.4 cm×12.4 cm×104.4 cm (when delivering max. tidal volume at min. pressure).

The operational mass is about 10 to 12 kg (water+cylinder weight=7.73 kg plus structure/valves/tubes). The operational water volume needed is 2.66 L when delivering maximum pressure (min. tidal volume) and is 7.73 L when delivering maximum tidal volume (min. delivery pressure).

The available tidal volume has an inverse relationship with the delivery pressure. The available PEEP range is 0 to 53 $cmH_2O$ if the PEEP tube terminates in the main reservoir. The available tidal volume range (example setpoints; pressure & volume are analog adjustments) is 0 to 1,070 mL when delivered at 40 $cmH_2O$, is 0 to 3,070 mL when delivered at 20 $cmH_2O$, is 0 to 3,570 mL when delivered at 15 $cmH_2O$, is 0 to 4,070 mL when delivered at 10 $cmH_2O$, and is 0 to 4,570 mL when delivered at 5 $cmH_2O$.

Patient Ventilator Mask

In one example, the ventilator mask 120 of FIG. 1 is an existing mask modified to replace filters with valves. The mask may be connected to an inhalation line having an inhalation valve and an exhalation line having an exhalation valve. It can maintain a net positive pressure in the plenum between the mask and the patient's nose and mouth. It allows low-pressure breathing air to enter the plenum as dictated either by a controller (e.g., mandatory breathing operation) or by cues from the patient (e.g., on-demand breathing operation). It allows air to be exhaled through a separate valve, either by the predetermined control schedule (e.g., mandatory breathing) or by cues from the patient (e.g., on-demand breathing). It allows the patient to inhale and exhale freely in the event of a control failure or external valve system failure.

In one embodiment, a commercially available mask is modified to have the above features. The mask has attached filters. In its respirator mode, the user inhales air through the filters and exhales air through a central valve. Alternate or new filters can be purchased and reinstalled.

In the modified ventilator mask, one of the inlet non-return valves is defeated by removing the flapper valve from inside the mask. This now becomes the exhale port and is opened and closed by a downstream solenoid valve and then vented, through an appropriate filter to the atmosphere. The original exhale valve is reversed by taking flapper valve from outside of the mask and re-fitting inside the mask. This valve now acts as an emergency inhale port in case of failure of the remaining inlet valve (e.g., a solenoid upstream of the respirator stays closed due to some failure). In normal operation, the positive pressure maintained in the plenum between the mask and the user's face keeps this emergency valve closed. The remaining inhale valve is left untouched. The two original filters of the respirator are removed and replaced by two ventilator valve adaptors.

To allow air tubes to be connected to the mask, an adapter connection is made using the pair of ventilator valve adaptors having proximal portions attached to the two original inhale ports. The ventilator valve adaptors have distal portions to be attached, via an inhalation port to an inhalation line having an inhalation valve and via an exhalation port to an exhalation gas line having an exhalation valve.

The manufacturing of the mask may involve printing PETG and more flexible materials, as well as PETG, PET, PLA, and ABS. The manufacturing process uses Ecoflex 0035 for the silicone mold and Task 8 resin for the mask. Another process uses Wiles April 12 version with Cheetah TPU. Yet another process is used to make a bunch of PLA's at 0.15 mm layer height, about 10 ABS, 6 or so PETG at 30% and about as many at 40, a few ABS at 30% infill and about as many 40%.

Controller

Figure 13:
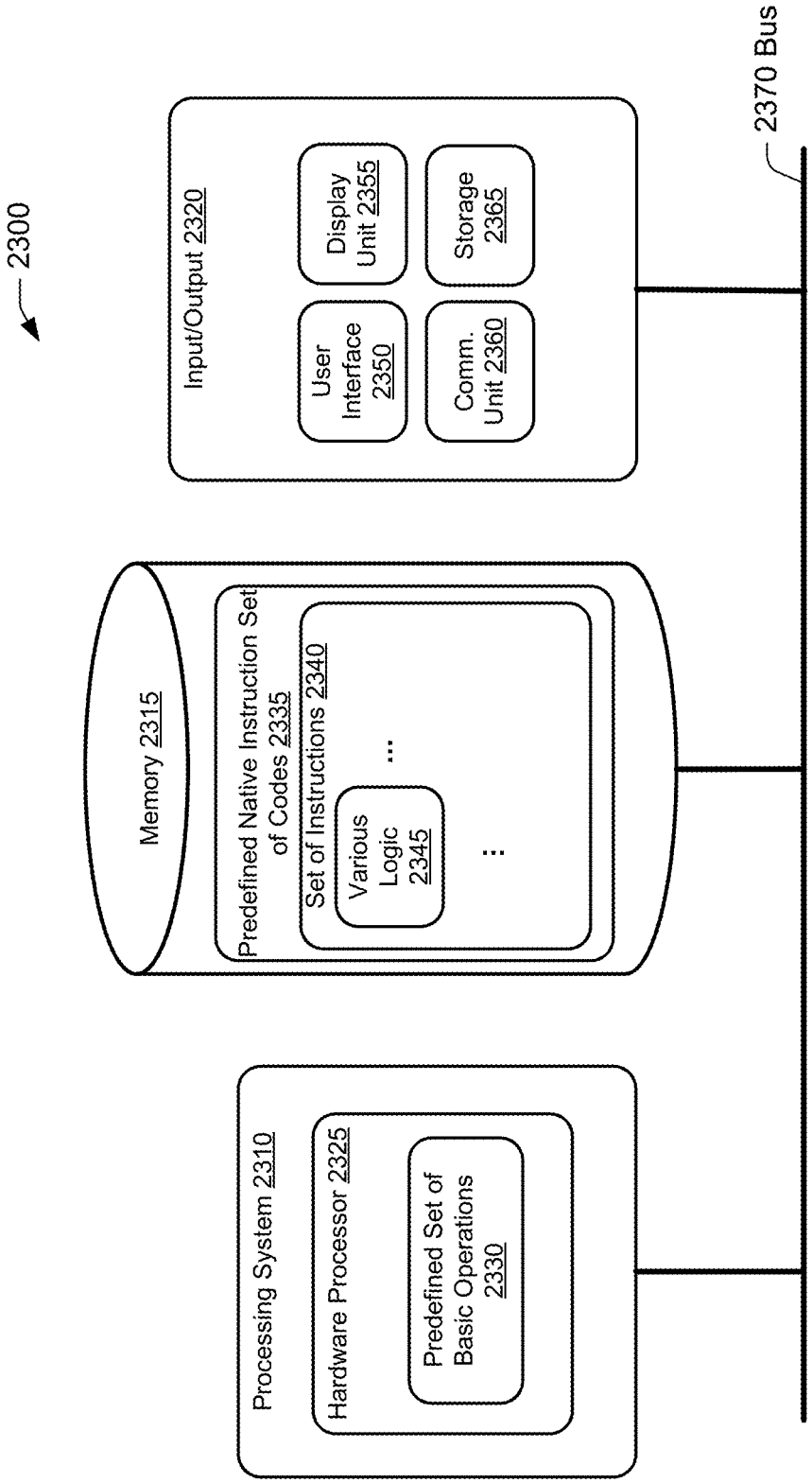
FIG. 13 illustrates an example of a controller or computing system including logic.

FIG. 13 illustrates an example of a controller or computing system 2300 including logic. The computing system 2300 includes a processing system 2310 having a hardware processor 2325 configured to perform a predefined set of basic operations 2330 by loading corresponding ones of a predefined native instruction set of codes 2335 as stored in the memory 2315. The computing system 2300 further includes input/output 2320 having user interface 2350, display unit 2355, communication unit 2360, and storage 2365.

The memory 2315 is accessible to the processing system 2310 via the bus 2370. The memory 2315 includes the predefined native instruction set of codes 2335, which constitute a set of instructions 2340 selectable for execution by the hardware processor 2325. In an embodiment, the set of instructions 2340 include logic 2345 to perform the functions of the ICHV apparatus as described above, including those summarized in the flow diagrams of FIG. 4.

The various logic 2345 is stored in the memory 2315 and comprises instructions 2340 selected from the predefined native instruction set of codes 2335 of the hardware processor 2325, adapted to operate with the processing system 2310 to implement the process or processes of the corresponding logic 2345.

In specific embodiments, the controller includes an Arduino controller and breadboard, several resistors and LEDs, a voltage regulator, and a potentiometer. These control system components are assembled and placed in a housing.

FIGS. 14A-14G show an example of controller logic for operating an ICHV system according to an embodiment of the invention. It is noted that this example of the controller logic does not include the breath timing function. An additional feature that can be added is to provide a user setting specifying the mandatory breath frequency in terms of breaths-per-minute.

The inventive concepts taught by way of the examples discussed above are amenable to modification, rearrangement, and embodiment in several ways. For example, the embodiments shown employ an inverted inner cylindrical container and an upright outer cylindrical container, each having a uniform cross-section. In other embodiments, the inverted inner container or the upright outer container or both may be non-cylindrical with nonuniform cross-sections and/or nonuniform cross-sectional areas along the height direction, or may be non-cylindrical with a uniform cross-sectional area. The calculations of volumes, pressures, and heights will be different as a result, but the apparatus operates on the same principles.

Some embodiments of the ICHV system present low-tech, easy-to-fabricate arrangements to provide breathing gas to a patient's mask. The required inputs include: 1) compressed breathing gas supply, 2) electricity for microcontroller, UV light, and heating element, and 3) distilled water. If only ambient air is available (i.e., no compressed breathing gas supply is available to supply breathing gas into a gas volume of the inverted cylinder space), a linear drive unit can be used to lift the inverted cylinder and a one-way valve is provided to allow atmospheric air to enter into the gas volume of the inverted cylinder space.

Accordingly, although the present disclosure has been described with reference to specific embodiments and examples, persons skilled in the art will recognize that changes may be made in form and detail without departing from the spirit and scope of the disclosure.

Certain attributes, functions, steps of methods, or sub-steps of methods described herein may be associated with physical structures or components, such as a module of a physical device that, in implementations in accordance with this disclosure, make use of instructions (e.g., computer executable instructions) that are embodied in hardware, such as an application specific integrated circuit, computer-readable instructions that cause a computer (e.g., a general-purpose computer) executing the instructions to have defined characteristics, a combination of hardware and software such as processor implementing firmware, software, and so forth so as to function as a special purpose computer with the ascribed characteristics. For example, in embodiments a module may comprise a functional hardware unit (such as a self-contained hardware or software or a combination thereof) designed to interface the other components of a system such as through use of an API. In embodiments, a module is structured to perform a function or set of functions, such as in accordance with a described algorithm. This disclosure may use nomenclature that associates a component or module with a function, purpose, step, or sub-step to identify the corresponding structure which, in instances, includes hardware and/or software that function for a specific purpose. For any computer-implemented embodiment, "means plus function" elements will use the term "means;" the terms "logic" and "module" and the like have the meaning ascribed to them above, if any, and are not to be construed as means.

The claims define the invention and form part of the specification. Limitations from the written description are not to be read into the claims.

An interpretation under 35 U.S.C. § 112(f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features and/or methodological steps, it is to be understood that the subject matter defined in the appended claims is not necessarily limited to the specific features or steps described. Rather, the specific features and steps are disclosed as example forms of implementing the claimed subject matter. To the extent headings

What is claimed is:

1. A ventilator comprising:
an outer container having a closed bottom and an open top to contain a liquid inside the outer container;
an inverted container having a closed top and an open bottom, the open bottom of the inverted container being submerged in the liquid of the outer container to provide an inner container liquid level inside the inverted container and an outer container liquid level between the inverted container and the outer container, the inverted container including an inverted container wall surrounded by an outer container wall of the outer container, the open bottom of the inverted container being spaced from the closed bottom of the outer container by an elevation which is variable, the inverted container having an inverted container space between the closed top and the inner container liquid level, the inner container liquid level and the outer container liquid level being measured relative to the closed bottom of the outer container;
a gas supply line to supply a breathing gas to the inverted container space; and
an inhalation line having an inhalation inlet in the inverted container space and an inhalation outlet outside of the liquid and the inverted container to provide the breathing gas from the inverted container space to a patient;
the inverted container being configured to move upward from a first elevation position when the breathing gas in the inverted container space reaches a hydrostatic delivery pressure and to continue moving upward while a volume of the inverted container space increases, the inverted container being configured to stop moving upward and the gas supply line being configured to stop supplying the breathing gas to the inverted container space when the inverted container reaches a second elevation position; and
the inhalation line being configured to open to permit a flow of the breathing gas from the inhalation inlet in the inverted container space to the inhalation outlet coupled to the patient, lowering the elevation of the inverted container.

2. The ventilator of claim 1,
wherein the inhalation line is configured to close and the gas supply line is configured to supply the breathing gas to the inverted container space when the inverted container has reached the first elevation position lower than the second elevation position, lifting the elevation of the inverted container.

3. The ventilator of claim 1,
wherein the inhalation line is configured to open to permit the flow of the breathing gas from the inhalation inlet in the inverted container space to the inhalation outlet coupled to the patient, lowering the elevation of the inverted container, based on one of (1) detection of a patient breath demand signal or (2) a first preset timing.

4. The ventilator of claim 3, further comprising:
an exhalation line having an exhalation inlet to receive exhaled gas from the patient and an exhalation outlet disposed in the liquid between the inverted container wall and the outer container wall at a fixed elevation relative to the closed bottom of the outer container, the fixed elevation being at a submerged depth measured from the outer container liquid level of the liquid and being selected to set a target hydrostatic backpressure.

5. The ventilator of claim 4,
wherein when the inverted container has reached the first elevation position, the exhalation line is opened to permit an exhalation gas flow from the patient through the exhalation inlet to the exhalation outlet disposed in the liquid between the inverted container wall and the outer container wall, the gas supply line supplies the breathing gas to flow to the inverted container space, lifting the elevation of the inverted container.

6. The ventilator of claim 5,
wherein based on one of (1) detection of the target hydrostatic backpressure at the exhalation outlet or (2) a second preset timing, the exhalation line is configured to be closed to stop the exhalation gas flow from the exhalation inlet to the exhalation outlet in the liquid at the fixed elevation.

7. The ventilator of claim 6, further comprising:
an inhalation sensor coupled with the inhalation line to detect the patient breath demand signal;
a first elevation sensor to detect when the inverted container reaches the first elevation position; and
a second elevation sensor to detect when the inverted container reaches the second elevation position.

8. The ventilator of claim 1, further comprising:
an inhalation valve disposed in the inhalation line and being configured to be opened to permit the breathing gas to flow from the inhalation inlet to the inhalation outlet or be closed to block the breathing gas from flowing from the inhalation inlet to the inhalation outlet; and
an exhalation valve disposed in an exhalation line and being configured to be opened to permit an exhalation gas to flow from an exhalation inlet to an exhalation outlet or be closed to block the exhalation gas from flowing from the exhalation inlet to the exhalation outlet.

9. The ventilator of claim 8, further comprising:
a bubbler disposed in the liquid below the inverted container space, wherein the gas supply line has a gas supply outlet terminating at the bubbler to form bubbles that flow up to the inverted container space;
a bubbler bypass line coupled between the gas supply line and the inhalation line to direct the breathing gas to bypass the bubbler and flow from the gas supply line via the inhalation line to the inverted container space; and
a bubbler bypass valve disposed in the bubbler bypass line and being configured to be closed to direct the breathing gas to flow to the gas supply outlet terminating at the bubbler or to be opened to direct the breathing gas to bypass the bubbler and flow to the inverted container space.

10. The ventilator of claim 8,
wherein the inhalation line and the exhalation line merge, at a junction downstream of the inhalation valve and upstream of the exhalation valve, into a single patient breathing line to be coupled to the patient.

11. A method of supporting breathing of a patient, the method comprising:
placing an inverted container having a closed top and an open bottom in an outer container having a closed bottom and an open top and containing a liquid inside the outer container, the open bottom of the inverted container being submerged in the liquid of the outer container to provide an inner container liquid level inside the inverted container and an outer container liquid level between the inverted container and the outer container, the inverted container including an inverted container wall surrounded by an outer container wall of the outer container, the open bottom of the inverted container being spaced from the closed bottom of the outer container by an elevation which is variable, the inverted container having an inverted container space between the closed top and the liquid, the inner container liquid level and the outer container liquid level being measured from the closed bottom of the outer container;
supplying a breathing gas via a gas supply line to the inverted container space, the inverted container configured to move upward from a first elevation position when the breathing gas in the inverted container space reaches a hydrostatic delivery pressure and to continue moving upward while a volume of the inverted container space increases, the inverted container being configured to stop moving upward and the gas supply line being configured to stop supplying the breathing gas to the inverted container space when the inverted container reaches a second elevation position;
placing an inhalation line having an inhalation inlet in the inverted container space and an inhalation outlet outside of the liquid and the inverted container to provide the breathing gas from the inverted container space to the patient; and
opening the inhalation line to permit a flow of the breathing gas from the inhalation inlet in the inverted container space to the inhalation outlet coupled to the patient, lowering the elevation of the inverted container.

12. The method of claim 11, further comprising:
closing the inhalation line and supplying the breathing gas via the gas supply line to the inverted container space when the inverted container has reached the first elevation position lower than the second elevation position, lifting the elevation of the inverted container.

13. The method of claim 11,
wherein the inhalation line is opened to permit the flow of the breathing gas from the inhalation inlet in the inverted container space to the inhalation outlet coupled to the patient, lowering the elevation of the inverted container, based on one of (1) detection of a patient breath demand signal or (2) a first preset timing.

14. The method of claim 13, further comprising:
placing an exhalation line having an exhalation inlet to receive exhaled gas from the patient and an exhalation outlet disposed in the liquid between the inverted container wall and the outer container wall at a fixed elevation relative to the closed bottom of the outer container, the fixed elevation being at a submerged depth measured from the outer container liquid level of the liquid and being selected to set a target hydrostatic backpressure.

15. The method of claim 14, further comprising:
when the inverted container has reached the first elevation position, opening the exhalation line to permit an exhalation gas flow from the patient through the exhalation inlet to the exhalation outlet disposed in the liquid between the inverted container wall and the outer container wall, and supplying the breathing gas via the gas supply line to the inverted container space, lifting the elevation of the inverted container.

16. The method of claim 15, further comprising:
based on one of (1) detection of the target hydrostatic backpressure at the exhalation outlet or (2) a second preset timing, closing the exhalation line to stop the exhalation gas flow from the exhalation inlet to the exhalation outlet in the liquid at the fixed elevation.

17. The method of claim 16, further comprising:
detecting the patient breath demand signal using an inhalation sensor coupled with the inhalation line;
detecting when the inverted container reaches the first elevation position using a first elevation sensor; and
detecting when the inverted container reaches the second elevation position using a second elevation sensor.

18. The method of claim 11, further comprising:
coupling an inhalation valve to the inhalation line, the inhalation valve being configured to be opened to permit the breathing gas to flow from the inhalation inlet to the inhalation outlet or be closed to block the breathing gas from flowing from the inhalation inlet to the inhalation outlet; and
coupling an exhalation valve to an exhalation line having an exhalation inlet to receive exhaled gas from the patient, the exhalation valve being configured to be opened to permit an exhalation gas to flow from the exhalation inlet to an exhalation outlet or be closed to block the exhalation gas from flowing from the exhalation inlet to the exhalation outlet.

19. The method of claim 18, further comprising:
connecting a bubbler to a gas supply outlet of the gas supply line, the bubbler being disposed in the liquid below the inverted container space to form bubbles from the breathing gas which flow up to the inverted container space;
coupling a bubbler bypass line between the gas supply line and the inhalation line to direct the breathing gas to bypass the bubbler and flow from the gas supply line via the inhalation line to the inverted container space; and
connecting a bubbler bypass valve to the bubbler bypass line, the bubbler bypass valve being configured to be closed to direct the breathing gas to flow to the gas supply outlet terminating at the bubbler or to be opened to direct the breathing gas to bypass the bubbler and flow to the inverted container space.

20. The method of claim 18, further comprising:
merging the inhalation line and the exhalation line, at a junction downstream of the inhalation valve and upstream of the exhalation valve, into a single patient breathing line to be coupled to the patient.

21. A ventilator comprising:
an outer container having a closed bottom and an open top to contain a liquid inside the outer container;
an inverted container having a closed top and an open bottom, the open bottom of the inverted container being submerged in the liquid of the outer container to provide an inner container liquid level inside the inverted container and an outer container liquid level between the inverted container and the outer container, the inverted container including an inverted container wall surrounded by an outer container wall of the outer container, the open bottom of the inverted container being spaced from the closed bottom of the outer container by an elevation which is variable, the inverted container having an inverted container space between the closed top and the liquid, the inner container liquid level and the outer container liquid level being measured from the closed bottom of the outer container;

means for directing a breathing gas to the inverted container space, to move the inverted container upward from a first elevation position when the breathing gas in the inverted container space reaches a hydrostatic delivery pressure, to continue moving the inverted container upward while a volume of the inverted container space increases, to stop moving the inverted container upward when the inverted container reaches a second elevation position higher than the first elevation position, and to move the inverted container upward at the hydrostatic delivery pressure when the inverted container drops from the second elevation position to the first elevation position; and an inhalation line having an inhalation inlet in the inverted container space and an inhalation outlet outside of the liquid and the inverted container to provide the breathing gas from the inverted container space to a patient.

22. The ventilator of claim 21,
wherein the inhalation line is configured to open to permit a flow of the breathing gas from the inhalation inlet in the inverted container space to the inhalation outlet coupled to the patient, lowering the elevation of the inverted container; and
wherein the inhalation line is configured to close when the inverted container has reached the first elevation position.

23. The ventilator of claim 21,
wherein the inhalation line is configured to open to permit a flow of the breathing gas from the inhalation inlet in the inverted container space to the inhalation outlet coupled to the patient, lowering the elevation of the inverted container, based on one of (1) detection of a patient breath demand signal or (2) a first preset timing.

24. The ventilator of claim 23, further comprising:
an exhalation line having an exhalation inlet to receive exhaled gas from the patient and an exhalation outlet disposed in the liquid between the inverted container wall and the outer container wall at a fixed elevation relative to the closed bottom of the outer container, the fixed elevation being at a submerged depth measured from the outer container liquid level of the liquid and being selected to set a target hydrostatic backpressure.

25. The ventilator of claim 24, further comprising:
means for directing an exhalation gas flow, when the inverted container has reached the first elevation position, to permit the exhalation gas flow from the patient through the exhalation inlet to the exhalation outlet disposed in the liquid between the inverted container wall and the outer container wall, and, based on one of (1) detection of the target hydrostatic backpressure at the exhalation outlet or (2) a second preset timing, to stop the exhalation gas flow from the exhalation inlet to the exhalation outlet in the liquid at the fixed elevation.

* * * * *